(12) United States Patent
Borgstrom et al.

(10) Patent No.: US 7,985,244 B2
(45) Date of Patent: Jul. 26, 2011

(54) POSTERIOR DYNAMIC STABILIZER DEVICES

(75) Inventors: Amie Borgstrom, North Attleborough, MA (US); SeungKyu Daniel Kwak, Grafton, MA (US); Missoum Moumene, Newton, MA (US); William Dunbar, Bethlehem, CT (US); John Riley Hawkins, Cumberland, RI (US)

(73) Assignee: DePuy Spine, Inc., Raynham, MA (US)

( * ) Notice: Subject to any disclaimer, the term of this patent is extended or adjusted under 35 U.S.C. 154(b) by 1548 days.

(21) Appl. No.: 11/162,873

(22) Filed: Sep. 27, 2005

(65) Prior Publication Data
US 2006/0084991 A1    Apr. 20, 2006

Related U.S. Application Data

(63) Continuation-in-part of application No. 10/955,207, filed on Sep. 30, 2004.

(51) Int. Cl.
*A61B 17/70* (2006.01)

(52) U.S. Cl. .......................... 606/249; 606/250

(58) Field of Classification Search ........... 606/246–279
See application file for complete search history.

(56) References Cited

U.S. PATENT DOCUMENTS

| | | | |
|---|---|---|---|
| 3,648,691 A | 3/1972 | Lumb et al. |
| 3,693,616 A | 9/1972 | Roaf et al. |
| 4,448,191 A | 5/1984 | Rodnyansky et al. |
| 4,743,260 A | 5/1988 | Burton |
| 5,084,049 A | 1/1992 | Asher et al. |
| 5,092,866 A | 3/1992 | Beard |
| 5,152,303 A | 10/1992 | Allen |
| 5,176,680 A | 1/1993 | Vignaud et al. |
| 5,190,543 A | 3/1993 | Schlapfer |
| 5,261,911 A | 11/1993 | Carl |
| 5,282,863 A | 2/1994 | Burton |
| 5,290,312 A | 3/1994 | Kojimoto et al. |
| 5,306,275 A | 4/1994 | Bryan |
| 5,360,429 A | 11/1994 | Jeanson et al. |
| 5,375,823 A | 12/1994 | Navas et al. |
| 5,387,213 A | 2/1995 | Breard et al. |
| 5,403,316 A | 4/1995 | Ashman |
| 5,415,661 A | 5/1995 | Holmes |
| 5,425,732 A | 6/1995 | Ulrich et al. |
| 5,437,669 A | 8/1995 | Yuan et al. |

(Continued)

FOREIGN PATENT DOCUMENTS

EP     0576379 A1     12/1993

(Continued)

OTHER PUBLICATIONS

EP Search Report, Application No. 05849737.1, Aug. 6, 2009.

(Continued)

*Primary Examiner* — Eduardo C Robert
*Assistant Examiner* — Mary Hoffman
(74) *Attorney, Agent, or Firm* — Nutter McClennen & Fish LLP

(57) ABSTRACT

A posterior stabilization device is provided for controlling movement between adjacent vertebrae. In one exemplary embodiment, the stabilization device can include one or more joints that rely on rotational or sliding movement to allow flexion of adjacent vertebrae, and that control extension, lateral bending, axial rotation, and anterior-posterior shear, preferably by providing one or more flexible connectors and/or a flexible central spacer for connecting to the adjacent superior and inferior vertebrae.

16 Claims, 14 Drawing Sheets

U.S. PATENT DOCUMENTS

| | | |
|---|---|---|
| 5,437,671 A | 8/1995 | Lozier et al. |
| 5,474,086 A | 12/1995 | McCormick et al. |
| 5,486,174 A | 1/1996 | Fournet-Fayard et al. |
| 5,496,318 A | 3/1996 | Howland et al. |
| 5,540,688 A | 7/1996 | Navas |
| 5,556,431 A | 9/1996 | Buttner-Janz |
| 5,562,737 A | 10/1996 | Graf |
| 5,571,191 A | 11/1996 | Fitz |
| 5,591,165 A | 1/1997 | Jackson |
| 5,601,554 A | 2/1997 | Howland et al. |
| 5,672,175 A | 9/1997 | Martin |
| 5,681,312 A | 10/1997 | Yuan et al. |
| 5,716,355 A | 2/1998 | Jackson et al. |
| 5,725,582 A | 3/1998 | Bevan et al. |
| 5,733,284 A | 3/1998 | Martin et al. |
| 5,755,796 A | 5/1998 | Ibo et al. |
| 5,766,254 A | 6/1998 | Gelbard |
| 5,810,815 A | 9/1998 | Morales et al. |
| RE36,221 E | 6/1999 | Breard et al. |
| 5,928,233 A | 7/1999 | Apfelbaum et al. |
| 5,938,663 A | 8/1999 | Petreto |
| 5,961,516 A | 10/1999 | Graf |
| 6,019,760 A | 2/2000 | Metz-Stavenhagen et al. |
| RE36,758 E | 6/2000 | Fitz |
| 6,132,464 A | 10/2000 | Martin |
| 6,241,730 B1 | 6/2001 | Alby |
| 6,248,106 B1 | 6/2001 | Ferree |
| 6,267,764 B1 | 7/2001 | Elberg |
| 6,273,888 B1 | 8/2001 | Justis |
| 6,355,038 B1 | 3/2002 | Pisharodi |
| 6,364,883 B1 | 4/2002 | Santilli |
| 6,419,703 B1 | 7/2002 | Fallin |
| 6,440,169 B1 | 8/2002 | Elberg et al. |
| 6,468,276 B1 | 10/2002 | McKay |
| 6,547,790 B2 | 4/2003 | Harkey |
| 6,551,322 B1 | 4/2003 | Lieberman |
| 6,551,332 B1 | 4/2003 | Nguyen et al. |
| 6,554,831 B1 | 4/2003 | Rivard et al. |
| 6,554,832 B2 | 4/2003 | Shluzas |
| 6,565,605 B2 | 5/2003 | Goble |
| 6,579,319 B2 | 6/2003 | Goble |
| 6,610,091 B1 | 8/2003 | Reiley |
| 6,626,904 B1 | 9/2003 | Jammet et al. |
| 6,626,909 B2 | 9/2003 | Chin |
| 6,626,944 B1 | 9/2003 | Taylor |
| 6,645,207 B2 | 11/2003 | Dixon et al. |
| 6,669,729 B2 | 12/2003 | Chin |
| 6,811,567 B2 | 11/2004 | Reiley |
| 7,011,685 B2 | 3/2006 | Arnin et al. |
| 7,074,237 B2 | 7/2006 | Goble et al. |
| 7,104,992 B2 | 9/2006 | Bailey |
| 7,189,236 B2 | 3/2007 | Taylor et al. |
| 7,270,665 B2 | 9/2007 | Morrison et al. |
| 7,276,069 B2 * | 10/2007 | Biedermann et al. ......... 606/250 |
| 2002/0029039 A1 | 3/2002 | Zucherman et al. |
| 2002/0055740 A1 | 5/2002 | Lieberman |
| 2002/0065557 A1 | 5/2002 | Goble et al. |
| 2002/0072800 A1 | 6/2002 | Goble et al. |
| 2002/0123806 A1 | 9/2002 | Reiley |
| 2002/0133155 A1 | 9/2002 | Ferree |
| 2002/0151978 A1 | 10/2002 | Zacouto et al. |
| 2003/0004572 A1 | 1/2003 | Goble et al. |
| 2003/0028250 A1 | 2/2003 | Reiley et al. |
| 2003/0055427 A1 | 3/2003 | Graf |
| 2003/0083657 A1 | 5/2003 | Drewry |
| 2003/0093078 A1 | 5/2003 | Ritland |
| 2003/0109880 A1 | 6/2003 | Shirado et al. |
| 2003/0135277 A1 | 7/2003 | Bryan et al. |
| 2003/0153912 A1 | 8/2003 | Graf |
| 2003/0171749 A1 | 9/2003 | Le Couedic et al. |
| 2003/0171750 A1 | 9/2003 | Chin |
| 2003/0176926 A1 | 9/2003 | Boehm et al. |
| 2003/0187438 A1 | 10/2003 | Assaker et al. |
| 2003/0187454 A1 | 10/2003 | Gill et al. |
| 2003/0191470 A1 | 10/2003 | Ritland |
| 2003/0191532 A1 | 10/2003 | Goble et al. |
| 2003/0220642 A1 | 11/2003 | Freudiger |
| 2003/0220643 A1 | 11/2003 | Ferree |
| 2004/0002708 A1 | 1/2004 | Ritland |
| 2004/0006391 A1 | 1/2004 | Reiley |
| 2004/0015174 A1 | 1/2004 | Null et al. |
| 2004/0049189 A1 | 3/2004 | Le Couedic et al. |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0073215 A1 | 4/2004 | Carli |
| 2004/0097950 A1 | 5/2004 | Foley et al. |
| 2004/0111154 A1 | 6/2004 | Reiley |
| 2004/0116927 A1 | 6/2004 | Graf |
| 2004/0127989 A1 | 7/2004 | Dooris et al. |
| 2004/0133203 A1 | 7/2004 | Young et al. |
| 2004/0138660 A1 | 7/2004 | Serhan |
| 2004/0143264 A1 | 7/2004 | McAfee |
| 2004/0147928 A1 | 7/2004 | Landry et al. |
| 2004/0186475 A1 | 9/2004 | Falahee |
| 2004/0186575 A1 | 9/2004 | Varga et al. |
| 2004/0236329 A1 | 11/2004 | Panjabi |
| 2004/0249379 A1 | 12/2004 | Winslow et al. |
| 2004/0267259 A1 | 12/2004 | Mazda et al. |
| 2005/0033431 A1 | 2/2005 | Gordon et al. |
| 2005/0033432 A1 | 2/2005 | Gordon et al. |
| 2005/0033434 A1 | 2/2005 | Berry |
| 2005/0033439 A1 | 2/2005 | Gordon et al. |
| 2005/0049708 A1 | 3/2005 | Atkinson et al. |
| 2005/0055096 A1 | 3/2005 | Serhan et al. |
| 2005/0085815 A1 * | 4/2005 | Harms et al. ................ 606/61 |
| 2005/0101954 A1 | 5/2005 | Simonson |
| 2005/0101956 A1 | 5/2005 | Simonson |
| 2005/0113927 A1 | 5/2005 | Malek |
| 2005/0119748 A1 | 6/2005 | Reiley et al. |
| 2005/0131409 A1 | 6/2005 | Chervitz et al. |
| 2005/0171610 A1 | 8/2005 | Humphreys et al. |
| 2005/0203518 A1 | 9/2005 | Biedermann et al. |
| 2005/0228381 A1 | 10/2005 | Kirschman |
| 2005/0228501 A1 | 10/2005 | Miller et al. |
| 2005/0240265 A1 | 10/2005 | Kuiper et al. |
| 2005/0245929 A1 * | 11/2005 | Winslow et al. ............. 606/61 |
| 2005/0256578 A1 | 11/2005 | Blatt et al. |
| 2005/0277922 A1 | 12/2005 | Trieu et al. |
| 2005/0277930 A1 | 12/2005 | Parsons |
| 2006/0036240 A1 * | 2/2006 | Colleran et al. ............. 606/61 |
| 2006/0052785 A1 | 3/2006 | Augostino et al. |
| 2006/0079896 A1 | 4/2006 | Kwak et al. |
| 2006/0084976 A1 | 4/2006 | Borgstrom et al. |
| 2006/0084982 A1 | 4/2006 | Kim |
| 2006/0084984 A1 | 4/2006 | Kim |
| 2006/0084991 A1 | 4/2006 | Borgstrom et al. |
| 2006/0129239 A1 | 6/2006 | Kwak |
| 2006/0149229 A1 | 7/2006 | Kwak et al. |
| 2006/0149230 A1 | 7/2006 | Kwak et al. |
| 2006/0189983 A1 | 8/2006 | Fallin et al. |
| 2006/0200130 A1 | 9/2006 | Hawkins et al. |
| 2006/0241771 A1 | 10/2006 | Gordon et al. |
| 2006/0265074 A1 | 11/2006 | Krishna et al. |
| 2006/0271046 A1 | 11/2006 | Kwak et al. |

FOREIGN PATENT DOCUMENTS

| | | |
|---|---|---|
| EP | 0669109 | 2/1994 |
| EP | 0612507 A1 | 8/1994 |
| EP | 0669109 A1 | 8/1995 |
| EP | 1153577 | 11/2001 |
| FR | 2694182 A | 2/1994 |
| FR | 2694182 A1 | 2/1994 |
| FR | 2697428 A1 | 5/1994 |
| FR | 2701833 A1 | 9/1994 |
| WO | 0145576 A1 | 6/2001 |
| WO | WO-01/45576 | 6/2001 |
| WO | 0217803 A2 | 3/2002 |
| WO | WO-02/17803 | 3/2002 |
| WO | 0243603 A1 | 6/2002 |
| WO | WO-02/43603 | 6/2002 |

| | | |
|---|---|---|
| WO | 02102259 | 12/2002 |
| WO | WO-02/102259 | 12/2002 |
| WO | 03007828 A1 | 1/2003 |
| WO | WO-03/007828 | 1/2003 |
| WO | 03009737 A1 | 2/2003 |
| WO | WO-03/009737 | 2/2003 |
| WO | 2004024011 A1 | 3/2004 |
| WO | WO-2004/024011 | 3/2004 |
| WO | 2004034916 A1 | 4/2004 |
| WO | WO-2004/034916 | 4/2004 |

OTHER PUBLICATIONS

EP Search Report ,Application No. 05849737.1, Aug. 6, 2009.

* cited by examiner

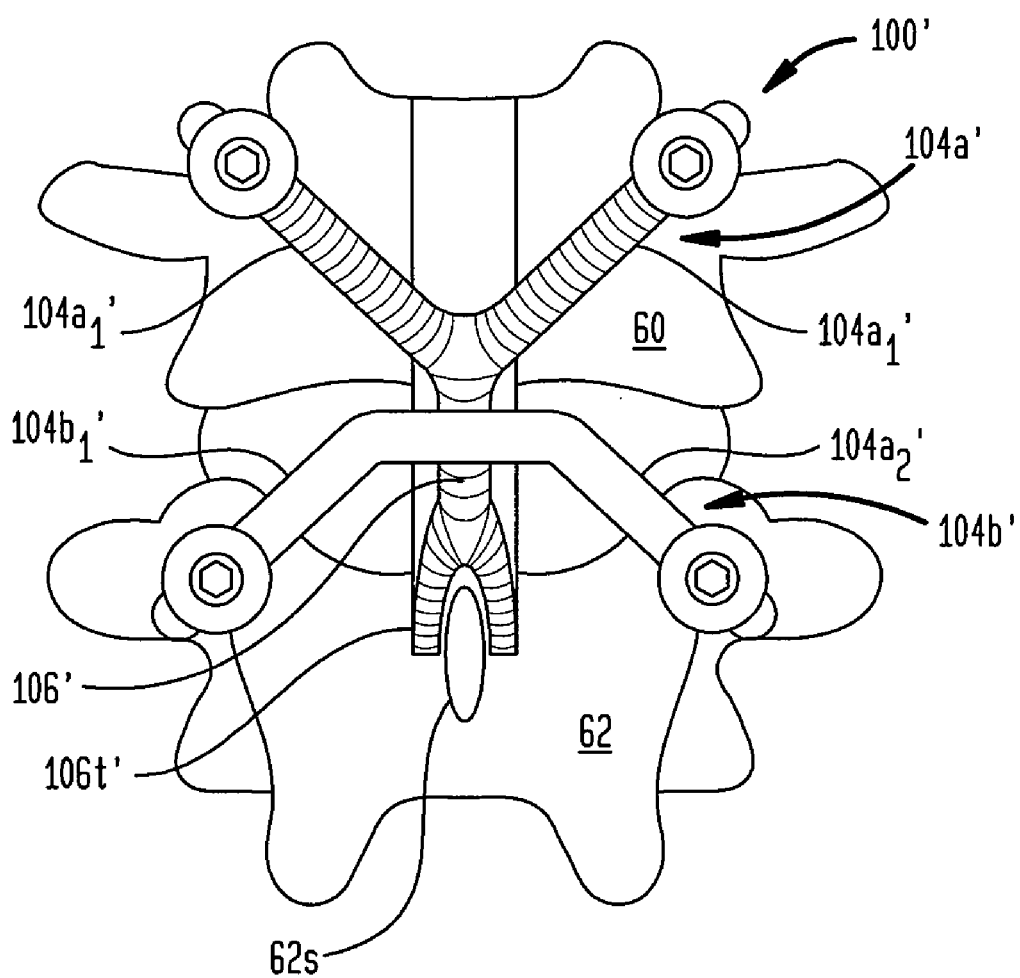

POSTERIOR DYNAMIC STABILIZER DEVICES

CROSS REFERENCE TO RELATED APPLICATIONS

This application is a continuation-in-part of U.S. patent application Ser. No. 10/955,207 filed on Sep. 30, 2004 and entitled "Posterior Stabilization Systems And Methods," which is hereby incorporated by reference in its entirety.

FIELD OF THE INVENTION

The present invention relates to spinal instrumentation, and in particular to various devices that are adapted to mimic the natural function of the structural posterior elements.

BACKGROUND OF THE INVENTION

The vertebrae in a patient's spinal column are linked to one another by the disc and the facet joints, which control movement of the vertebrae relative to one another. Each vertebra has a pair of articulating surfaces located on the left side, and a pair of articulating surfaces located on the right side, and each pair includes a superior articular surface, which faces upward, and an inferior articular surface, which faces downward. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to restore function to the three joint complex. Damaged, diseased levels in the spine were traditionally fused to one another. While such a technique may relieve pain, it effectively prevents motion between at least two vertebrae. As a result, additional stress may be applied to the adjoining levels, thereby potentially leading to further damage.

More recently, techniques have been developed to restore normal function to the facet joints. One such technique involves covering the facet joint with a cap to preserve the bony and articular structure. Capping techniques, however, are limited in use as they will not remove the source of the pain in osteoarthritic joints. Caps are also disadvantageous as they must be available in a variety of sizes and shapes to accommodate the wide variability in the anatomical morphology of the facets. Caps also have a tendency to loosen over time, potentially resulting in additional damage to the joint and/or the bone support structure containing the cap.

Other techniques for restoring the normal function to the posterior element involve arch replacement, in which superior and inferior prosthetic arches are implanted to extend across the vertebra typically between the spinous process. The arches can articulate relative to one another to replace the articulating function of the facet joints. One drawback of current articulating facet replacement devices, however, is that they require the facet joints to be resected. Moreover, alignment of the articulating surfaces with one another can be challenging.

Accordingly, there remains a need for improved systems and methods that are adapted to mimic the natural function of the facet joints.

BRIEF SUMMARY OF THE INVENTION

The present invention provides various methods and devices for repairing and/or replacing a damaged facet joint, and optionally for replacing other posterior elements, including, for example, the lamina, the posterior ligaments, and/or other features of a patient's spinal column. In one exemplary embodiment, an implantable device for replacing and/or stabilizing one or more facet joints in a patient's spinal column is provided and it generally includes at least one dynamic stabilizing member, e.g., a flexible member, and at least one stabilizing rod or connector that is adapted to couple to adjacent vertebrae and that is adapted to extend through the at least one flexible member. In an exemplary embodiment, the device includes superior and inferior connector members that are adapted to mate to superior and inferior vertebrae, respectively, and the flexible member(s) is adapted to span across at least two adjacent vertebrae in a patient's spinal column. In use, the superior and inferior connectors and the flexible member(s) are effective to control movement between the superior and inferior vertebrae. More preferably, the connector(s) are adapted to slidably and/or rotatably move relative to the flexible member(s), preferably without deforming the flexible member(s), when the adjacent vertebrae are moved within a first range of motion, and they are preferably adapted to deform the flexible member(s) when the adjacent vertebrae are moved within a second range of motion beyond the first range of motion.

The flexible member(s) can have a variety of configurations, shapes, and sizes. In one embodiment, the implant includes two flexible members and each flexible member has a substantially elongate shape. The flexible members can also have a shape that is in the form of an hour-glass. In another embodiment, the implant can include a single flexible member, and the flexible member can optionally have a shape that is substantially in the form of an hour-glass. The flexible member(s) can also have an elasticity that varies. For example, the flexible member can have a central portion that has an elasticity that is greater than an elasticity of opposed superior and inferior terminal ends thereof. In another embodiment, each flexible member can include at least two thru-bores formed therein for receiving the superior and inferior connectors therethrough. Each thru-bore can include a bushing or bearing disposed therein and adapted to receive a connector. The region surrounding the thru-bores can have properties or characteristics that vary, or that are at least different than the properties of the central region. In one embodiment, a region surrounding each thru-bore is adapted to provide stability to the connector extending therethrough. As such, each region surrounding the thru-bores can be substantially rigid or have less elasticity than the central portion.

Each connector can also have a variety of configurations, and in one embodiment each connector is in the form of a substantially rigid rod. More preferably, the superior connector includes opposed terminal ends that are adapted to couple to the pedicles of the superior vertebra, and a mid-portion that is adapted to extend around and be positioned inferior to the spinous process of the superior vertebra, and the inferior connector includes opposed terminal ends that are adapted to couple to the pedicles of the inferior vertebra, and a mid-portion that is adapted to be positioned proximate and superior to the spinous process of the inferior vertebra. In an exemplary embodiment, the superior connector is substantially v-shaped and the inferior connector is generally linear with a v-shaped portion formed therein. More preferably, the v-shaped superior connector includes a central linear portion and first and second lateral arms extending at an angle relative to the central linear portion, and the v-shaped portion in the inferior connector is preferably formed at a substantial midpoint thereof. In use, the v-shaped portion of the inferior connector can be adapted to fit around the spinous process of the inferior vertebra, and the v-shaped superior connector can be adapted to extend around the spinous process of the superior vertebra. Each connector can also include first and second terminal ends that are adapted to be fixedly mated to opposed sides of a vertebra. By way of non-limiting example, a spinal anchor, such as a spinal screw, can be used to fixedly a terminal end of a connector to the vertebra.

The present invention also provides methods for replacing and/or stabilizing the posterior elements in adjacent vertebrae. In one embodiment, the method can include the steps of coupling at least one flexible member to two adjacent vertebrae with at least one connector such that the at least one connector is slidably and/or rotatably movable relative to the at least one flexible member, preferably without substantially deforming the flexible member, when the vertebrae are moved within a first range of motion, and such that the at least one connector is effective to stretch and/or deform the at least one flexible member when the vertebrae are moved within a second range of motion beyond the first range of motion. Preferably, the step of coupling at least flexible member to two adjacent vertebrae with at least one connector comprises coupling a superior connector to a superior vertebra, and coupling an inferior connector to an inferior vertebra. The superior connector and the inferior connector can extend through first and second flexible members. In one embodiment, the superior and inferior connectors can be coupled to the superior and inferior vertebrae, respectively, by implanting first and second spinal anchors in each of the superior and inferior vertebra and locking the superior and inferior connectors to the spinal anchors.

In yet another embodiment, a method for restoring normal function to the posterior elements and/or replacing the posterior elements of adjacent vertebrae in a patient's spinal column is provided and it includes the steps of implanting a first pair of spinal anchors in opposed pedicles of a first vertebra, implanting a second pair of spinal anchors in opposed pedicles of an adjacent second vertebra, coupling opposed terminal ends of a first rigid member to the first pair of spinal anchors in the first vertebra, and coupling opposed terminal ends of a second rigid member to the second pair of spinal anchors in the second vertebra. The first and second rigid members preferably extend through at least one flexible member. In an exemplary embodiment, the first and second rigid members extend through first and second flexible members that are preferably positioned on opposed sides of a spinous process of each vertebra.

The method can also include the step of implanting a third pair of spinal anchors in opposed pedicles of a third vertebra adjacent to the second vertebra, coupling opposed terminal ends of a third rigid member to the second pair of spinal anchors in the second vertebra, and coupling opposed terminal ends of a fourth rigid member to the third pair of spinal anchors in the third vertebra. The third and fourth rigid members preferably extend through the at least one flexible member.

In another exemplary embodiment, a spinal stabilization device is provided having first and second connectors that are adapted to couple to first and second adjacent vertebrae. At least a portion of at least one of the first and second connectors can be elastically deformable to allow controlled lateral bending, axial rotation, and anterior-posterior shear between first and second adjacent vertebrae coupled thereto. The stabilization device can also include a linkage that is adapted to movably couple the first and second connectors to allow flexion of first and second adjacent vertebrae mated to the first and second connectors.

The connector(s) can have a variety of configurations, but in one exemplary embodiment the device includes a first connector with opposed arms that mate to a first vertebra, and a second connector with opposed arms that mate to a second vertebra. At least one of the first and second connectors can have substantially curved arms that are adapted to mate to opposed lateral sides of a vertebra. One or more of the arms of one or both connectors can also have a variety of configurations for providing controlled movement of the adjacent vertebrae. For example, the opposed arms of at least one of the connectors can include an elastically deformable portion. The elastically deformable portion can have a variety of shapes and sizes, and can, for example, have a symmetrical or asymmetrical cross-sectional geometry. The device can also include a cross-connector that is adapted to mate to opposed arms of at least one of the first and second connectors.

The linkage can also have a variety of configurations. In one embodiment, the linkage can be configured to allow the first and second connectors to rotate relative to one another. For example, the linkage can be in the form of at least one rotating joint formed between the first and second connectors. Alternatively, the linkage can be adapted to allow the first and second connectors to slide relative to one another. For example, the linkage can be in the form of a sliding joint formed between the first and second connectors. In another embodiment, the linkage can be in the form of a central spacer that is coupled to the first and second connectors, and more preferably that is rotatably mated to the first and second connectors by first and second hinge joints. The hinge joints can be formed, for example, by a first bore formed in the central spacer for rotatably receiving the first connector, and a second bore formed in the central spacer for rotatably receiving the second connector. The hinge joints can also be configured to be spaced a distance apart from one another in an anterior-posterior direction when the device is implanted.

In yet another embodiment, a spinal stabilization device is provided having a central spacer that is adapted to be positioned between posterior elements of adjacent vertebrae, and at least one connector that is movably coupled to the central spacer and that is adapted to couple to adjacent vertebrae. At least one of the central spacer and the connector(s) can be rigid, and the other one of the central spacer and the connector(s) can be flexible such that the device is configured to allow flexion, and to control extension, lateral bending, axial rotation, and anterior-posterior shear of adjacent vertebrae coupled thereto. In an exemplary embodiment, the device includes a first connector having opposed arms adapted to couple to opposed lateral sides of a first vertebra, and a second connector having opposed arms adapted to couple to opposed lateral sides of a second vertebra. A first bearing surface can be formed between the first connector and the central spacer for allowing rotational movement of the first connector relative to the central spacer, and a second bearing surface can be formed between the second connector and the central spacer for allowing rotational movement of the second connector relative to the central spacer.

The present invention also provides exemplary methods for stabilizing adjacent vertebrae. In one embodiment, a stabilization device can be coupled to adjacent superior and inferior vertebrae, and at least one joint on the stabilization device can be limited to movement during at least one of flexion and extension of the adjacent vertebrae, and at least one connector on the stabilization device can be configured to elastically deform to control lateral bending, axial rotation, and anterior-posterior shear of the adjacent vertebrae. The device can be used in conjunction with the natural disc, or in other embodiments it can be used with an artificial disc replacement.

BRIEF DESCRIPTION OF THE DRAWINGS

The invention will be more fully understood from the following detailed description taken in conjunction with the accompanying drawings, in which:

FIG. 9E is a posterior view of another embodiment of a spinal stabilization device having a spinous process stop formed thereon;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides various methods and devices for stabilizing the posterior elements of the spine, and more preferably for sharing the load with the intervertebral disc, the facet joints, the ligaments, and the muscles of the spinal column. The methods and devices can also stabilize and protect the facet joints in the lumbar spine, as well as other posterior spinal muscles and ligaments. Methods and devices are also provided for replacing damaged, injured, diseased, or otherwise unhealthy posterior elements, such as the facet joints, the lamina, the posterior ligaments, and/or other features of a patient's spinal column. In one exemplary embodiment, the methods and devices are effective to mimic the natural function of the spine by providing resistance during flexion, extension, lateral bending, axial rotation, and/or anterior-posterior shear. In one embodiment, the device can allow a high degree of flexibility between two adjacent vertebrae when the vertebrae are moved within a first range of motion, and by controlling or limiting movement of the adjacent vertebrae within a second range of motion beyond the first range of motion. In another embodiment, sliding and/or rotating joints can be used to control movement of adjacent vertebrae. The methods are devices can be used with the natural disc or with an artificial disc replacement. In certain exemplary embodiments, the methods and devices can be adapted to substantially control or provide resistance to movement, e.g., flexion, extension, lateral bending, and/or axial rotation, of at least two adjacent vertebrae. The methods and devices can also be adapted for minimally invasive use. A person skilled in the art will appreciate that, while the methods and devices are especially configured for use in restoring and/or replacing the facet joints and optionally other posterior elements of a patient's spine, the methods and devices can be used for a variety of other purposes in a variety of other surgical procedures.

Figure 1A:
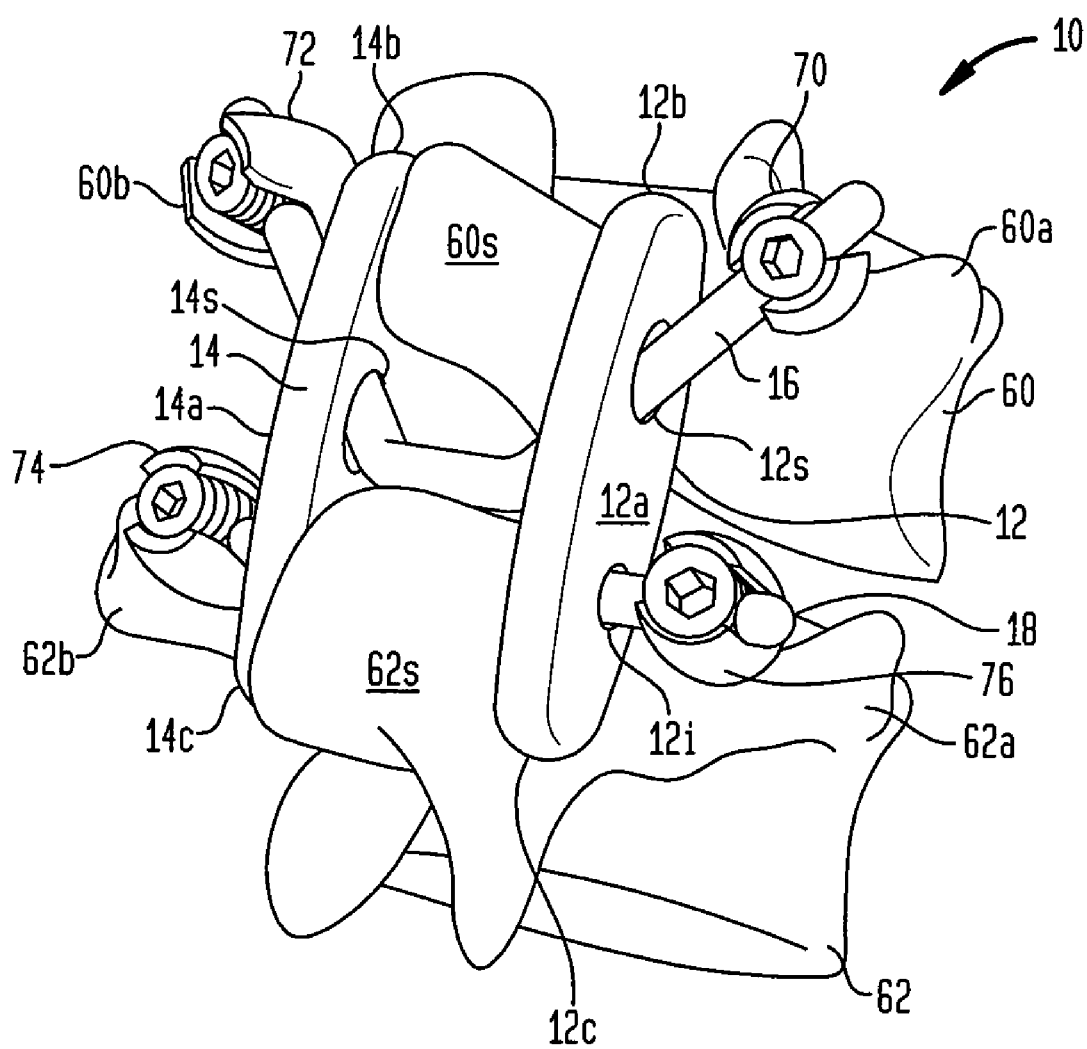
FIG. 1A is a perspective view illustration of two adjacent vertebrae coupled to one another by a facet joint stabilizing device in accordance with one embodiment of the present invention.
Figure 1B:
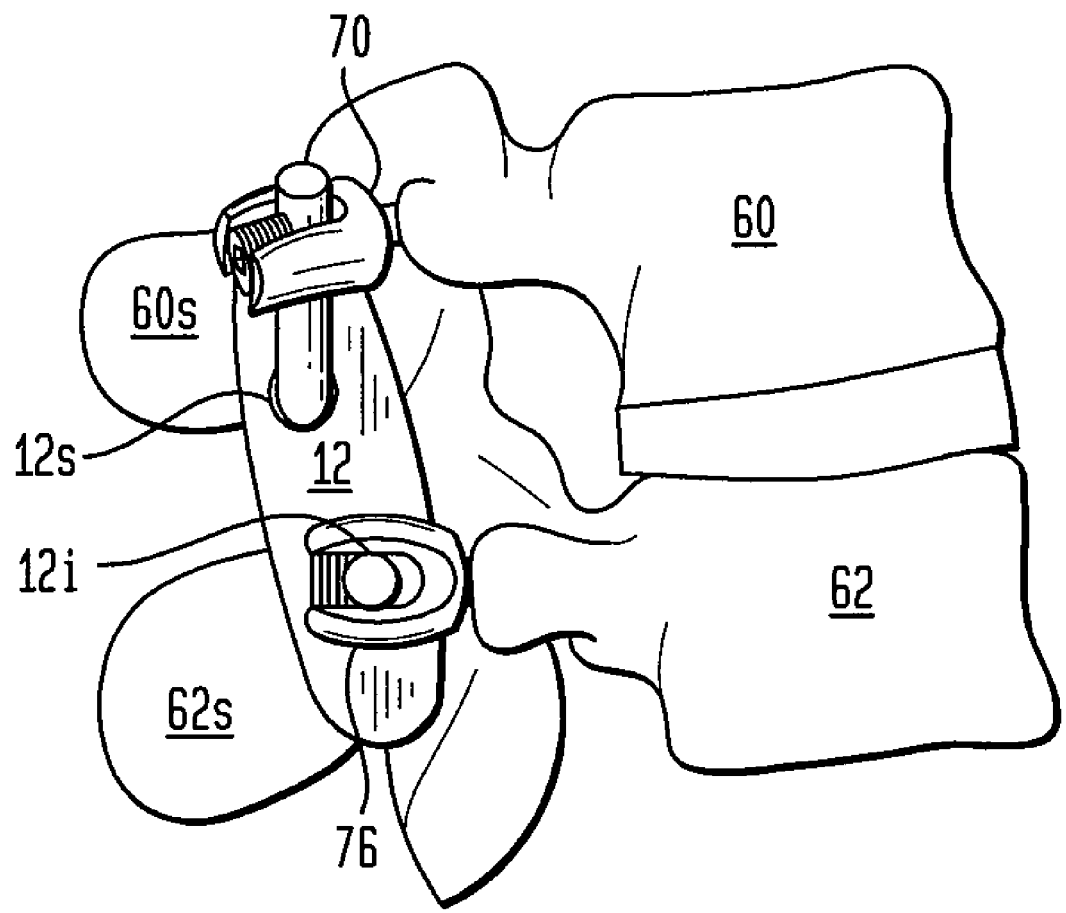
FIG. 1B is a side view illustration of the vertebrae and device shown in FIG. 1A.
Figure 1C:
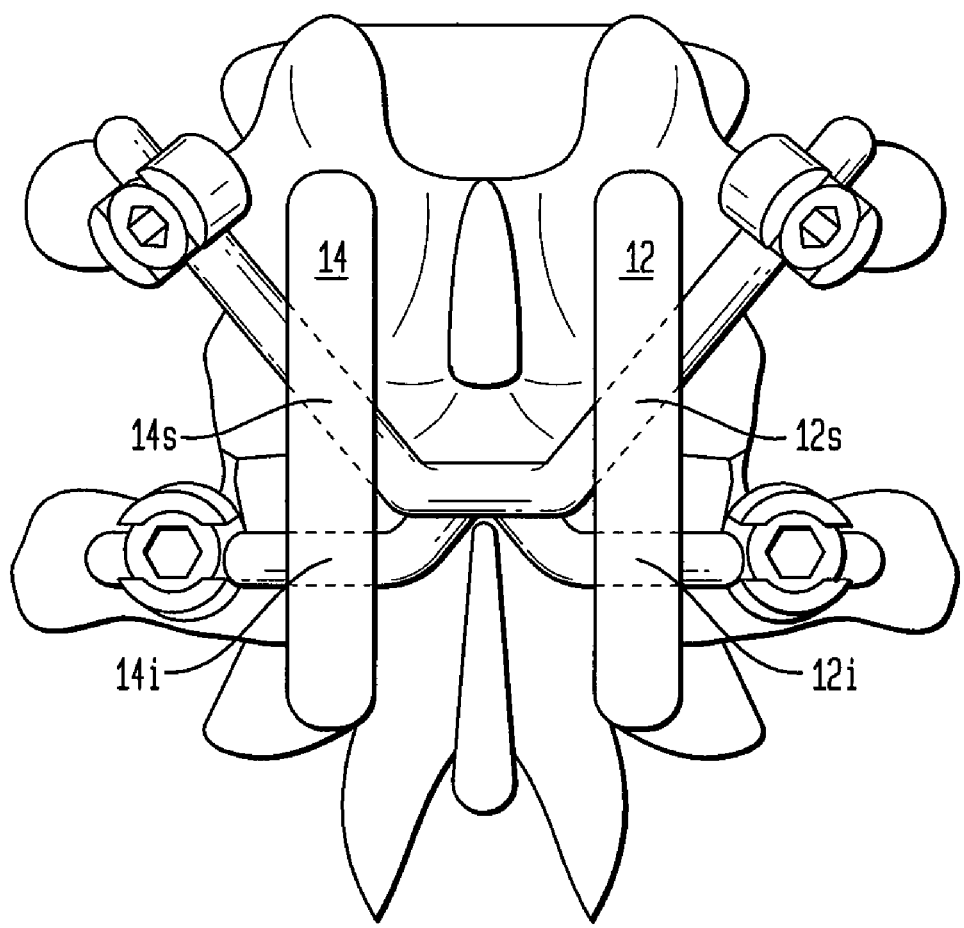
FIG. 1C is a front view illustration of the vertebrae and device shown in FIG. 1A.

FIGS. 1A-1C illustrate one exemplary embodiment of a posterior element replacement implant connected between adjacent vertebrae 60, 62. As shown, the implant 10 generally includes first and second flexible members 12, 14, also referred to as dynamic stabilizing elements, and first and second connectors 16, 18, also referred to as stabilizing rods. The implant 10 is preferably effective to mimic the natural function of the spine. As shown in FIGS. 1A-1C, the implant 10 is coupled to superior and inferior vertebrae 60, 62 such that it is effective to perform the function of the posterior elements that connect the vertebrae, or to otherwise control movement of the vertebrae 60, 62. More particularly, the first connector 16, hereinafter referred to as the superior connector 16, is coupled to the superior vertebra 60, and the second connector 18, hereinafter referred to as the inferior connector 18, is coupled to the inferior vertebra 62. The superior and inferior connectors 16, 18 extend through the first and second flexible members 12, 14, such that the connectors 16, 18 are coupled to one another via the flexible members 12, 14. As a result, the connectors 16, 18 and the flexible members 12, 14 are effective to control movement of the vertebrae 60, 62 relative to one another, thereby functioning in place of the posterior elements. In an exemplary embodiment, the flexible members 12, 14 are movable, e.g., rotatable and/or slidable, but preferably not deformable, relative to at least one of the connectors, e.g., the superior connector 16, when the vertebrae 60, 62 are moved within a first range of motion, and at least one of the connectors, e.g., the superior connector 16, is effective to deform, e.g., stretch, rotate, etc., the flexible members 12, 14, or otherwise create resistance, when the superior and inferior vertebrae 60, 62 are moved within a second range of motion beyond the first range of motion.

Figure 4:
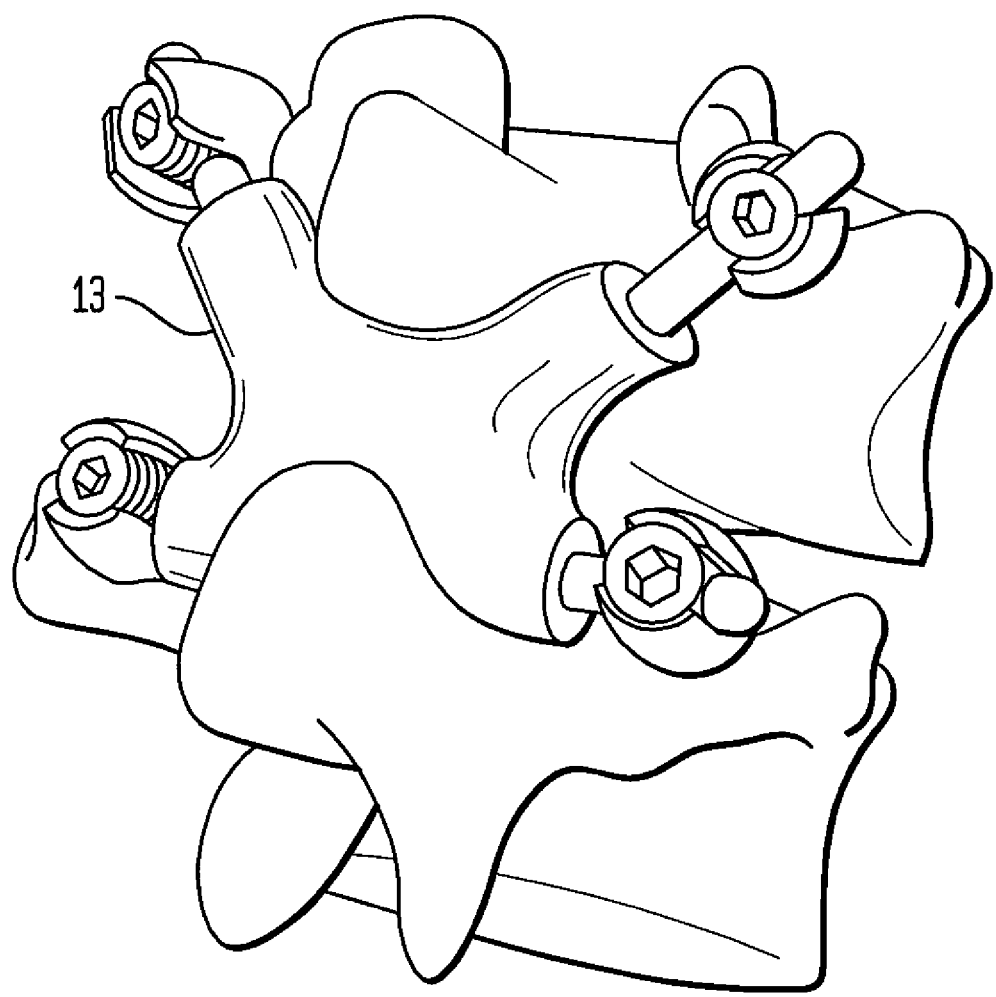
FIG. 4 is a perspective view of another embodiment of a posterior element stabilizing device in accordance with the present invention.

A person skilled in the art will appreciate that while FIGS. 1A-1C illustrate two flexible members 12, 14 and two connectors 16, 18, that any number of flexible members can be used. By way of non-limiting example, the implant 10 can include only one flexible member that is similar to flexible member 12 or 14. In another embodiment, shown in FIG. 4, the implant can include a single flexible member 13 that performs the function of flexible members 12 and 14. More particularly, the single flexible member 13 can have an hourglass shape such that the narrow region of the hour glass extends between the spinous process of two adjacent vertebrae, and the widened ends of the hour glass extends at or adjacent to the location of the facet joints. This configuration is particularly useful in laminectomy procedures in which the spinous processes are removed. A person skilled in the art will also appreciate that the function of the flexible members 12, 14 and the connectors 16, 18 can be reversed. For example, the connectors 16, 18 can be formed from a flexible or deformable material, and members 12, 14 can be substantially rigid.

Each flexible member can have a variety of configurations, shapes, and sizes. In an exemplary embodiment, as shown, each flexible member 12, 14 has a generally elongate shape such that it is adapted to span across two or more adjacent vertebrae. While FIGS. 1A-1C illustrate substantially rectangular-shaped or oblong members 12, 14, in other exemplary embodiments the flexible members 12, 14 can have an oval shape, a cylindrical shape, etc. By way of non-limiting example, FIG. 2D illustrates two flexible members 12', 14' having an hour-glass shape. The length of the flexible members 12, 14 will vary depending on the number of levels being repaired and/or replaced, and thus the number of vertebrae to which the implant is to be attached to. As shown in FIGS. 1A-1C, each flexible member 12, 14 has a length that is adapted to span across two adjacent vertebrae 60, 62. The flexible members 12, 14 can also be adapted to be positioned on opposed sides of the spinous process, such that the flexible members 12, 14 can be positioned in or near the location of the facet joints, as is also shown in FIGS. 1A-1C.

Each flexible member 12, 14 also preferably includes at least one thru-bore formed therethrough for receiving the connectors 16, 18. As best shown in FIG. 1C, each flexible member 12, 14 includes a superior thru-bore 12s, 14s, and inferior thru-bore 12i, 14i. Each thru-bore 12s, 12i, 14s, 14i should have a size that is adapted to receive the connector 16, 18 therethrough preferably without allowing significant movement of the connector 16, 18 relative thereto, i.e., such that the connectors 16, 18 are in close contact with the thru-bores 12s, 12i, 14s, 14i. The thru-bores 12s, 12i, 14s, 14i are, however, preferably effective to allow at least one of the connectors 16, 18, and preferably both of the connectors 16, 18, to slide freely therethrough. Such a configuration allows the flexible members 12, 14 to slide along and/or rotate with respect to the connectors 16, 18, at least during a particular range of motion which will be discussed in more detail below.

Each thru-bore 12s, 12i, 14s, 14i can also be adapted to facilitate sliding and/or rotating movement of the flexible members 12, 14 relative to the connectors 16, 18. In an exemplary embodiment, the thru-bores 12s, 12i, 14s, 14i are preferably configured to prevent or reduce wearing thereof during use of the implant. While various techniques can be used to achieve this, in one exemplary embodiment each thru-bore 12s, 12i, 14s, 14i can include a bushing or bearing element disposed therein and adapted to slidably receive a connector 16, 18. In one exemplary embodiment, shown in FIG. 2C which illustrates flexible member 12, the superior thru-bore 12s can include a superior bushing 20s and the inferior thru-bore 12i can include an inferior bushing 20i. Each bushing 20s, 20i is in the form of a generally hollow, cylindrical member that is adapted to fit within the thru-bore 12s, 12i in the flexible member 12 and that functions as a bearing surface for the connectors 16, 18. The bushings 20s, 20i can, however, have virtually any shape and size.

In another embodiment (not shown), the flexible members 12, 14 can include a bearing surface formed within or integrally with the thru-bores 12s, 12i, 14s, 14, and/or the thru-bores 12s, 12i, 14s, 14i can at least be modified to achieve properties that will facilitate movement of the connectors 16, 18 relative thereto. Alternatively, the thru-bores 12s, 12i, 14s, 14i, or at least a region surrounding the thru-bores 12s, 12i, 14s, 14i, can have a stiffness that is greater than a remainder of the flexible members 12, 14, or at least that is sufficient to minimize wear on the thru-bores 12s, 12i, 14s, 14i when the device 10 is implanted and in use. The bushings 20s, 20i, the thru-bores 12s, 12i, 14s, 14i, or bearing surface formed within the thru-bores 12s, 12i, 14s, 14i can be formed from any material. Suitable materials include, by way of non-limiting example, metals, ceramics, polymers, etc. A person skilled in the art will appreciate that a variety of techniques can be used to facilitate slidable and/or rotatable movement of the flexible members 12, 14 relative to the connectors 16, 18.

Each flexible member 12, 14 can also be formed from a variety of materials, but each flexible member 12, 14 is preferably effective to mimic the flexion/extension, rotation, lateral bending, and load carrying requirements of the posterior elements of the spine. In an exemplary embodiment, each flexible member 12, 14 is formed from a polymer, and more preferably a biocompatible polymer, such as polyurethane, composite reinforced polyurethane, silicone, etc. A person skilled in the art will appreciate that the material can vary depending on the intended use. For example, a material can be selected, based on a patient's size and condition, to have a particular stiffness.

The properties of the flexible members 12, 14 can also vary, and they can be uniform or non-uniform throughout the body thereof. In one embodiment, each flexible member 12, 14 can have a mid-portion 12a, 14a that is more elastic than terminal ends 12b, 12c, 14b, 14c of the flexible members 12, 14. The flexible members 12, 14 can also have regions that are more or less elastic than the remainder of the member 12, 14. In one exemplary embodiment, the flexible members 12, 14 can be configured to have a first elasticity during the first range of motion, and a second, different elasticity in a second range of motion beyond the first range of motion, as will be discussed in more detail below. In another exemplary embodiment, as noted above, the regions surrounding the thru-bores 12s, 12i, 14s, 14i can be formed from a material having a stiffness that is greater than the remainder of the flexible members 12, 14.

The connectors 16, 18 of the implant 10 can also have a variety of configurations, but in an exemplary embodiment they are adapted to allow the flexible members 12, 14 to slide and/or rotate freely, preferably without deforming, relative thereto when the superior and inferior vertebrae 60, 62 are moved within a first range of motion, and they are adapted to deform the flexible members 12, 14 when the superior and inferior vertebrae 60, 62 are moved within a second range of motion beyond the first range of motion. While various techniques can be used to achieve such a configuration, FIGS. 1A-1C illustrate one exemplary embodiment of superior and inferior connectors 16, 18.

Figure 2A:
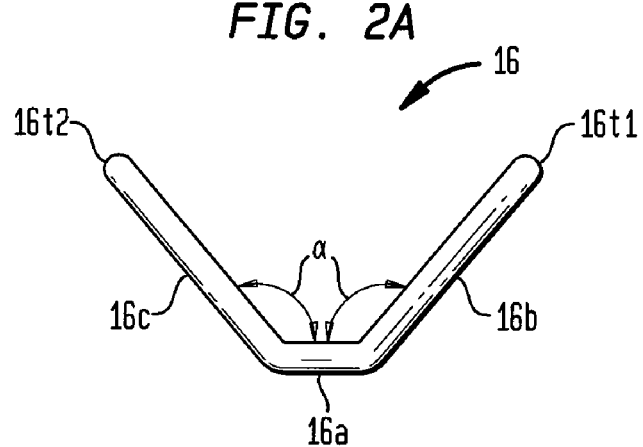
FIG. 2A is a side view illustration of the superior connector of the device shown in FIGS. 1A-1C.

The superior connector 16, which is shown in more detail in FIG. 2A, is preferably adapted to couple to opposed pedicles 60a, 60b (FIG. 1A) of the superior vertebra 60 and to extend between the pedicles 60a, 60b and inferior to the spinous process 60s. The configuration of the superior connector 16 can, however, change where a laminectomy is performed and the spinous process 60s has been removed. The connector 16 can, for example, be substantially linear. In the embodiment shown in FIG. 2A, the superior connector 16 is in the form of a substantially v-shaped rod and it preferably includes a central linear portion 16a with two lateral arms 16b, 16c extending at an angle $\alpha$ relative to the central portion 16a. The angle $\alpha$ can vary depending on the size of the patient, and in particular depending on the distance between the opposed pedicles 60a, 60b and the angle necessary to allow the superior connector 16 to extend around the spinous process 60s. The angle $\alpha$ is also determinative of the range of sliding motion between the flexible members 12, 14 and the connectors 16, 18. In particular, the range of motion of the flexible members 12, 14 along the connectors 16, 18 will increase as the angle increases. This will be discussed in more detail below. While the angle $\alpha$ can vary, in an exemplary embodiment, the angle $\alpha$ is in the range of about 95° to 180°.

Figure 2B:
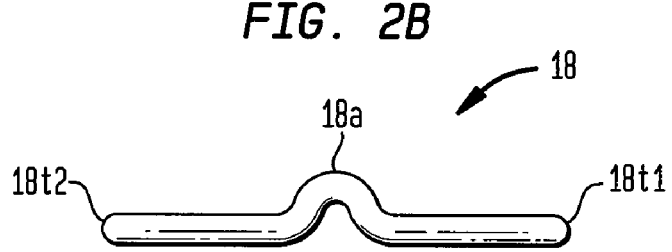
FIG. 2B is a side view illustration of the inferior connector of the device shown in FIGS. 1A-1C.
Figure 2C:
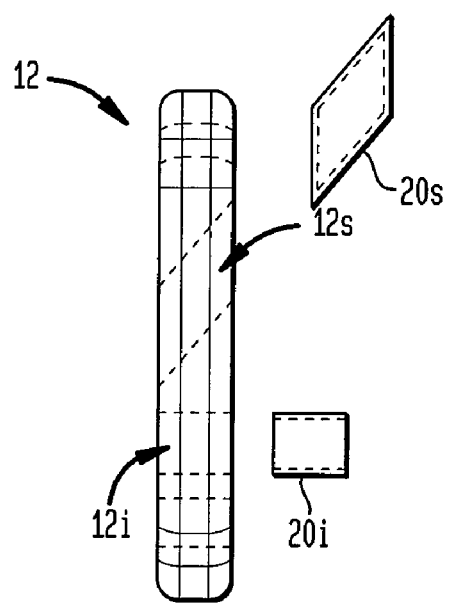
FIG. 2C is an exploded view illustration of one of the flexible members of the device shown in FIGS. 1A-1C.
Figure 2D:
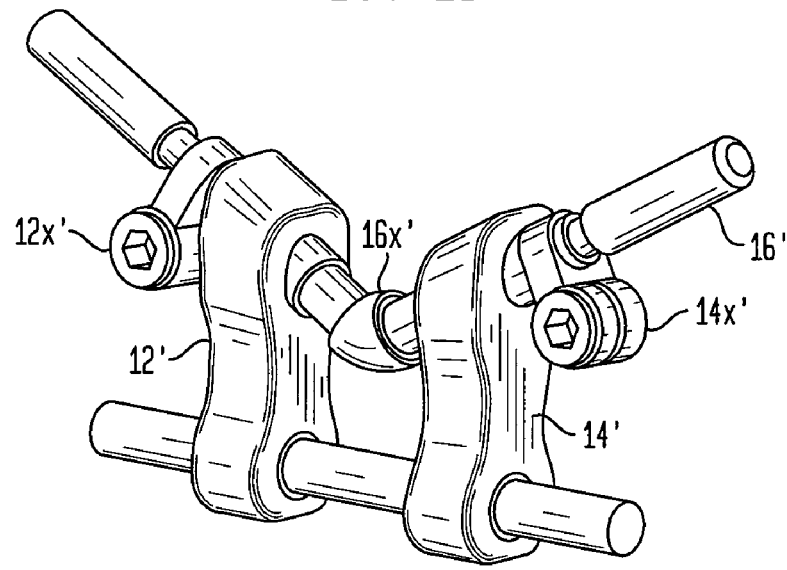
FIG. 2D illustrates another embodiment of a posterior element stabilizing device having hour-glass shaped flexible members.

The inferior connector 18, which is shown in more detail in FIG. 2B, is similarly adapted to couple to the opposed pedicles 62a, 62b (FIG. 1A) of the inferior vertebra 62 and to extend between the pedicles 62a, 62b ands superior to the spinous process 62s. The connector 18, however, preferably has a substantially linear configuration. In an exemplary embodiment, as shown in FIG. 2B, the connector 18 is in the form of a rod having a v-shaped portion 18a formed therein, preferably at a substantially central portion thereof. The v-shaped portion 18a is configured to extend around, and be positioned superior to the spinous process 62s of the vertebra 60.

Each connector 16, 18 can also be formed from a variety of materials, but preferably the connectors 16, 18 are substantially rigid. In an exemplary embodiment, the connectors 16, 18 are formed from a bioimplantable metal, such as titanium, stainless steel, and cobalt and nickel based alloys, such as cobalt-chromium-molybdenum (Co—Cr Mo).

In use, the implant 10 can be used to replace one or more of the posterior elements of the spine, including, for example, the facet joints, the lamina, the posterior ligaments, and/or other features of a patient's spinal column. The implant 10 can also be adapted to function with either a natural vertebral disc, or with an artificial disc. Regardless, as noted above, the implant 10 is preferably adapted to mimic the function of the posterior elements, without necessarily mimicking the anatomy. The device 10 is implanted by first positioning the superior and inferior connectors 16, 18 through the thru-bores 12s, 12i, 14s, 14i in the flexible members 12, 14. If necessary, other procedures, such as a facetectomy and/or laminectomy, can be performed. The terminal ends $16t_1$, $16t_2$, $18t_1$, $18t_2$ of the connectors 16, 18 are then attached to the superior and inferior vertebrae 60, 62. As noted above, the superior connector 16 is preferably attached to the opposed pedicles 60a, 60b on the superior vertebra 60, and the inferior connector 18 is preferably attached to the opposed pedicles 62a, 62b on the inferior vertebra 62.

The connectors 16, 18 can be attached to the vertebrae 60, 62 using a variety of anchoring devices and other techniques known in the art. In an exemplary embodiment, as shown in FIGS. 1A-1C, the connectors 16, 18 are attached to the vertebrae 60, 62 using spinal anchors, and in particular spinal screws. While only a portion of the spinal screws are shown, each screw includes a rod-receiving head 70, 72, 74, 76 that is configured to seat a terminal end $16t_1$, $16t_2$, $18t_1$, $18t_2$ of a connector 16, 18. A fastening element, such as a set screw, can be used to lock the connectors 16, 18 to the screws 70, 72, 74, 76.

While not shown, several additional connectors can be attached to adjacent vertebrae and positioned to extend through flexible members 16, 18, or through separate flexible members, thereby forming a multi-level replacement. The number of connectors, and optionally the number of flexible members, will vary depending on the number of levels being repaired. In attaching additional connectors, each pair of spinal anchors, e.g., spinal screws 70, 72, 74, 76, can be configured to mate to two connectors. Thus, for example, if a third vertebra, located inferior to the second vertebra 62, were coupled to the first and second vertebra 60, 62, a superior connector would mate to spinal anchors 74, 76, and an inferior connector would mate to spinal anchors disposed within the pedicles of the third vertebra. This procedure could be repeated for multiple vertebrae. While not shown, the procedure can also include the step of placing a sheath or protective member partially or fully around the implant 10 for preventing tissue from growing on the implant 10 and into the thru-bores 12s, 12i, 14s, 14i, and for preventing debris from migrating into the spinal canal.

Figure 3:
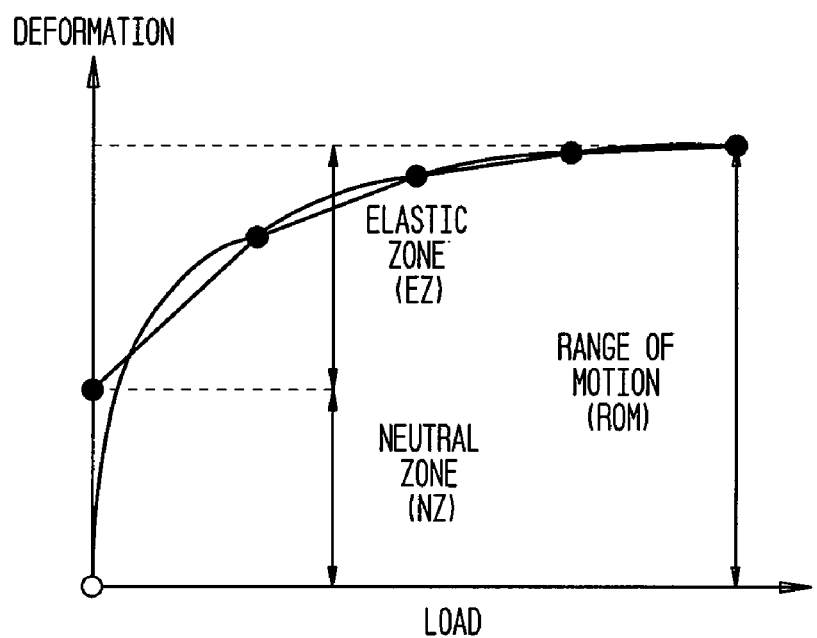
FIG. 3 is a chart showing a typical load-deformation curve of a human functional spine unit.

Once the connectors 16, 18 are fixedly attached to the vertebrae 60, 62, the implant 10 is effective to control movement of the vertebrae relative to one another. More particularly, the implant 10 is effective to mimic the natural function of the spine. FIG. 3 is a chart illustrating the load-deformation curve of a functional spine unit (FSU). As shown, the FSU is highly flexible at low loads, and it stiffens as the load increases. Thus, the FSU becomes much less flexible as the range of motion increases. To analyze this nonlinear biphasic behavior, the load-displacement curve is divided into two parts: (1) the neutral zone, in which the FSU is highly flexible, and (2) the elastic zone, in which the FSU is much less flexible, and has a high degree of stiffness. The two zones together constitute the physiological range of motion of a zone. The implant 10 is adapted to mimic this behavior. In particular, during flexion of the vertebrae 60, 62 relative to one another in the neutral zone, referred to herein as the first range of motion, the flexible members 12, 14 are free to slide along and/or rotate with respect to the connectors 16, 18.

Thus, as the vertebrae flex away from one another, while in the neutral zone, the connectors 16, 18 are moved apart from one another thereby causing the flexible members 12, 14 to move toward one another. Similarly, during extension, the flexible members 12, 14 are free to slide and/or rotate, however they will move apart from one another. Such movement is at least in part due to the shape of the connectors 16, 18, and in particular the v-shape of the superior connector 16. When the vertebrae 60, 62 are further flexed relative to one another in the elastic zone, referred to herein as the second range of motion (which is necessarily beyond than the first range of motion), the flexible members 12, 14 are forced to deform, which can include stretching, rotating, etc. This is a result of the shape of the connectors 16, 18, which prevent the flexible members 12, 14 from moving further toward one another. As a result, in the first range of motion, the implant 10 mimics the natural spine by allowing a greater degree of flexibility, as the connectors 16, 18 allow the flexible members 12, 14 to slide therealong and/or rotate relative thereto with minimal resistance, and in the second range of motion, the implant 10 mimics the natural spine by controlling flexibility, as the connectors 16, 18 cause the flexible members 12, 14 to deform, thereby resisting flexion. As discussed above, the properties of the flexible members 12, 14 will necessarily affect the resistance to flexion, and the flexible members 12, 14 can be especially adapted to have a first flexibility in the first range of motion and a second flexibility in the second range of motion. Since each patient's specific needs will vary, the implant 10 can be provided as part of a kit having several flexible members 12, 14 varying in shape, size, and stiffness. The flexible members 12, 14 can also be particularly tailored to different levels of a patient's spine.

The implant can also optionally include physical stops to control when the flexible members stop sliding and/or rotating and are forced to deform. In particular, the physical stops can be formed on or attached to the connectors 16, 18 at a location that will prevent the flexible members 12, 14 from sliding and/or rotating at a particular point during flexion of the vertebrae. By way of non-limiting example, FIG. 2D illustrates outer stops 12x', 14x' disposed on the superior connector 16' on opposed sides of the flexible members 12', 14'. A central stop 16x' is also formed on the connector 16' between the flexible members 12', 14'. The outer stops 12x', 14x' are in the form of band clamps which can be adjustably positioned at various locations along the connector 16'. The central stop 16x' is in the formed of a stepped member, and it can also optionally be adjustable. For example, the central stop 16x' can be in the form of a housing and the opposed sides of the connector 16' can thread into the housing. A person skilled in the art will appreciate that the stops can have any configuration and that a variety of other techniques can be used to control movement between the vertebrae in such a manner that mimics the natural function of the spine.

In the embodiments discussed above with respect to FIGS. 1A-4, the various stabilization devices each generally include one or more joints that connect the superior and inferior connectors. For example, in the embodiment shown in FIG. 1A, two joints are formed between the first flexible member 12 and the superior and inferior connectors 16, 18, and two joints are formed between the second flexible member 14 and the superior and inferior connectors 16, 18. The joints allow both sliding and rotational movement between the connectors to allow flexion and extension of the adjacent vertebrae. In another exemplary embodiment, rather than using joints that rely on both sliding and rotational movement, the posterior stabilization device can include one or more joints that rely solely on rotational or sliding movement to allow flexion of adjacent vertebrae. All other movement, i.e., extension, lateral bending, axial rotation, and anterior-posterior shear, can be allowed and preferably controlled by providing one or more flexible connectors and/or a flexible central spacer for connecting the adjacent superior and inferior vertebrae.

Figure 5A:
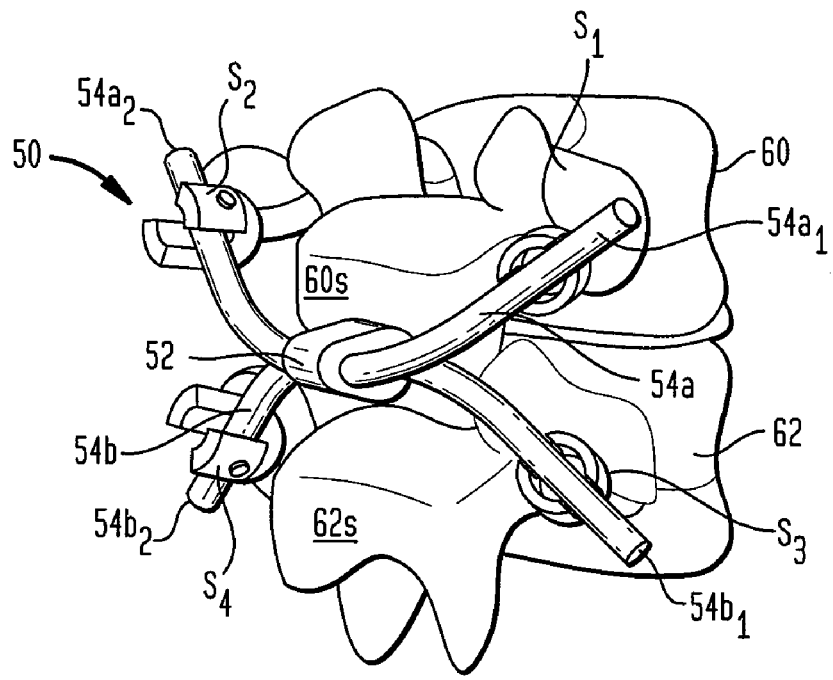
FIG. 5A is a posterio-lateral perspective view of two adjacent vertebrae coupled to one another by a spinal stabilization device having a central spacer with connectors rotatably coupled thereto in accordance with yet another exemplary embodiment.
Figure 5B:
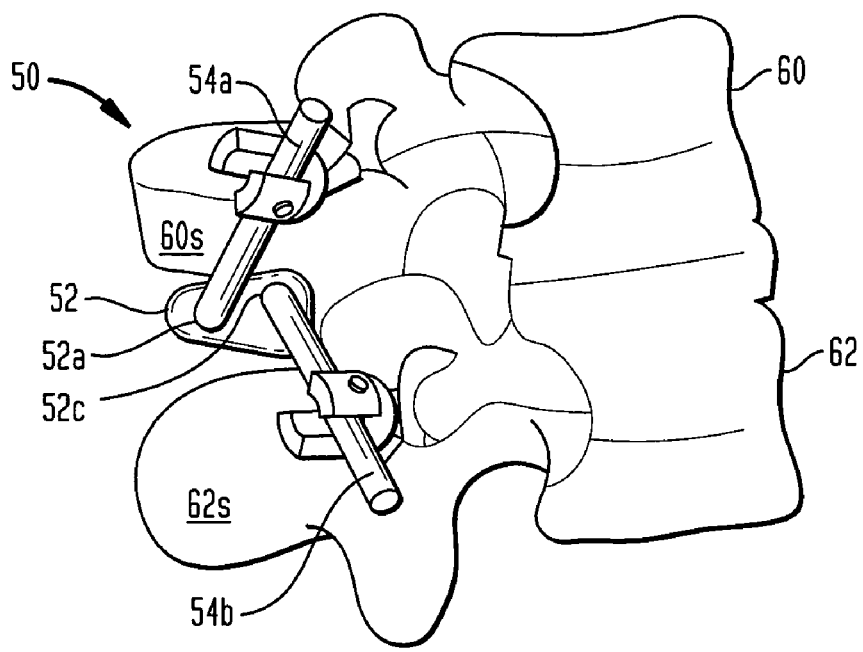
FIG. 5B is a side view of the spinal column and device shown in FIG. 5A.

FIGS. 5A and 5B illustrate one such exemplary embodiment. As shown, the spinal stabilization device 50 includes a first superior connector 54a that is configured to mate to a superior vertebra 60, and a second inferior connector 54b that is configured to mate to an adjacent inferior vertebra 62. A central spacer 52, which can be configured to be positioned between spinous processes 60s, 62s or other posterior elements of adjacent vertebrae 60, 62 in order to limit extension, is coupled to and forms a linkage between the first and second connectors 54a, 54b. In particular, as will be discussed in more detail below, a first joint is formed between the first connector 54a and the central spacer 52, and a second joint is formed between the second connector 54b and the central spacer 52. The first and second joints allow rotational movement of the opposed connectors 54a, 54b relative to the central spacer 52, thereby allowing flexion of the spine. The rotational or hinge joints can also allow extension to occur, however the central spacer 52 can limit extension by acting as a stop, or it can be flexible to provide resistance to extension. All other movement, i.e., lateral bending, axial rotation, and anterior-posterior shear, can be controlled by forming at least a portion of the connectors 54a, 54b and/or the central spacer 52 from a flexible or elastically deformable material such that the connectors 54a, 54b and/or the central spacer 52 provide resistance during such movement.

Each connector 54a, 54b can have a variety of configurations, and the particular configuration can vary depending on the desired degree of movement between the adjacent vertebrae 60, 62 coupled to the connectors 54a, 54b. In the illustrated embodiment, each connector 54a, 54b is substantially curved or U-shaped with opposed arms 54a₁, 54a₂, 54b₁, 54b₂ that are adapted to mate to opposed lateral sides of a vertebra 60, 62. More particularly, the shape of the connectors 54a, 54b can be configured to mate to the pedicles of adjacent vertebrae 60, 62 while a central portion of each connector 54a, 54b is positioned between the spinous processes 60s, 62s of the adjacent vertebrae 60, 62. This allows the central portion of each connector 54a, 54b to couple to one another by a linkage, such as the central spacer 52.

The connectors 54a, 54b can be formed from a substantially rigid material, such as a metal, or at least a portion of at least one of the connectors 54a, 54b can be flexible or elastically deformable such that the connectors 54a, 54b will bend or otherwise deform to allow lateral bending, axial rotation, and anterior-posterior shear to occur between the adjacent vertebrae 60, 62 coupled to the connectors 54a, 54b. The degree of flexibility or deformity can vary depending on the desired amount of movement, and a person skilled in the art will appreciate that the flexibility or elasticity can be selected to allow a controlled amount of movement to occur and in particular to provide a desired amount of resistance to movement. In an exemplary embodiment, each connector 54a, 54b is substantially rigid at the central portion and at the terminal ends of the arms 54a₁, 54a₂, 54b₁, 54b₂, and each connector 54a, 54b is flexible or elastic at the portions extending between the central portion and the terminal ends of the arms 54a₁, 54a₂, 54b₁, 54b₂. Such a configuration allows the connectors 54a, 54b to securely mate to the adjacent vertebrae 60, 62 and to the central spacer 52, yet provide a desired amount of controlled movement during use. Furthermore, one or both connectors 54a, 54b can include a shelf (not shown) protruding therefrom at a central portion thereof to limit the rotation of the central spacer 52. The shelf can also contact the spinous process to share the load applied to the central spacer 52.

As indicated above, the spinal stabilization device 50 can also include a central spacer 52 that is adapted to form a linkage between the connectors 54a, 54b. While the central spacer 52 can have virtually any configuration, in the illustrated exemplary embodiment the central spacer 52 is substantially wedge-shaped such that it is sized and configured to fit between the posterior elements, such as the spinous processes 60s, 62s, of the adjacent vertebrae 60, 62. If the spinous processes 60s, 62s, or other posterior elements have been removed or otherwise compromised (e.g., laminectomy), the shape of the central spacer 52 can be modified. For example, the central spacer 52 can be configured to be positioned adjacent to the remaining spinous process or in the space previously occupied by the removed spinous process. The central spacer 52 can also be formed from a variety of materials, and it can be rigid to function as a stop during extension, or it can be flexible or elastically deformable, i.e., compressible, such that the central spacer 52 provides resistance to extension or other movement of the adjacent vertebrae 60, 62. Where the spinous processes 60s, 62s have been removed or comprised, the central spacer 52 can include a mechanical stop added thereto to control extension.

The central spacer 52 can couple to the connectors 54a, 54b using a variety of techniques, including using rotational and/or sliding joints. In the illustrated embodiment, the central spacer 52 is configured to allow the connectors 54a, 54b to rotate relative thereto. As shown in FIG. 5B, a rotational joint is provided by two bores 52a, 52b formed through the central spacer 52 for receiving the connectors 54a, 54b. The bores 52a, 52b can be formed at various locations on the central spacer 52, however in the illustrated embodiment the central spacer 52 includes a posterior bore 52a extending laterally therethrough for receiving the superior connector 54a and an anterior bore 52b extending laterally therethrough for receiving the inferior connector 54b. As a result, the rotational joint between the superior connector 54a and the central spacer 52 is positioned posterior to the rotational joint between the inferior connector 54b and the central spacer 52. Such a configuration is particularly effective to ensure that the central spacer 52 remains properly positioned between the spinous processes 60s, 62s of the adjacent vertebrae 60, 62. A person skilled in the art will appreciate that the placement of the connectors 54a, 54b may be switched such that the posterior bore 52a receives the inferior connector 54b and the anterior bore 52b receives the superior connector 54a. The central spacer 52 can also be configured to prevent translation (sliding movement) of the connectors 54a, 54b relative thereto. This can be achieved by providing a tight fit between the central spacer 52 and the connectors 54a, 54b, or in other embodiments the bores 52a, 52b in the central spacer 52 can include bushings disposed therein to grip the connectors 54a, 54b. A person skilled in the art will appreciate that a variety of other techniques can be used to limit or prevent movement of the connectors 54a, 54b with respect to the central spacer 52.

Figure 6A:
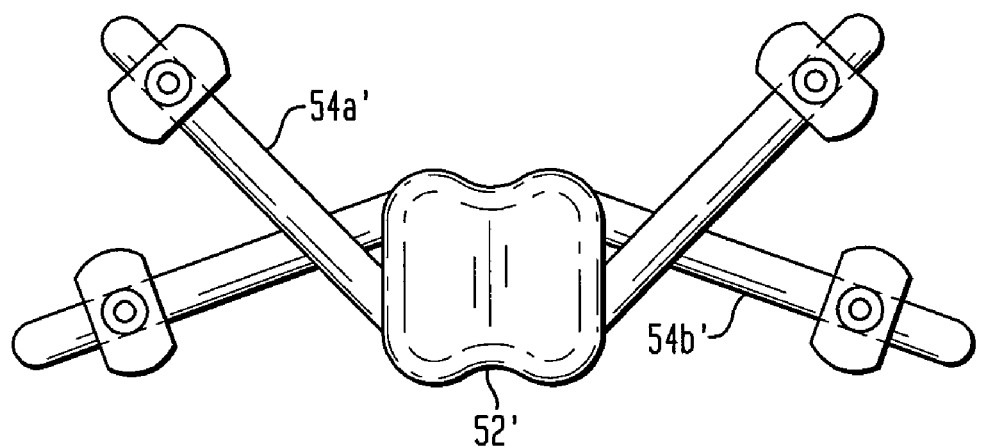
FIG. 6A is a posterior view of another embodiment of a spinal stabilization device for coupling to adjacent vertebrae.

In use, the central spacer 52 is positioned between the spinous processes 60s, 62s or between other posterior elements of adjacent vertebrae 60, 62. The connectors 54a, 54b can be pre-disposed through the central spacer 52, or they can be disposed through the central spacer 52 after the central spacer 52 is implanted. One or more bone-engaging elements, such as polyaxial bone screws, can be used to mate the arms $54a_1$, $54a_2$, $54b_1$, $54b_2$ of the connectors 54a, 54b to the superior and inferior vertebrae 60, 62. As shown in FIGS. 5A and 5B, four polyaxial bone screws $S_1$, $S_2$, $S_3$, $S_4$ are implanted in the pedicles of the adjacent vertebrae 60, 62, and the arms $54a_1$, $54a_2$, $54b_1$, $54b_2$ of the connectors 54a, 54b are fixedly mated thereto. Flexion of the adjacent vertebrae 60, 62 can cause the connectors 54a, 54b to rotate relative to the central spacer 52 and the central spacer 52 to rotate between the spinous processes 60s, 62s or other posterior elements as the connectors 54a, 54b move away from one another. Movement of the adjacent vertebrae 60, 62 can also cause the connectors 54a, 54b and/or the central spacer 52 to elastically bend or deform such that the connectors 54a, 54b and/or the central spacer 52 provide resistance to flexion, extension, lateral bending, axial rotation, and anterior/posterior shear, thereby controlling such movement. As is further shown, the central spacer 52 can be substantially cylindrical to facilitate rotation thereof between the spinous processes 60s, 62s of the adjacent vertebrae 60, 62 during flexion. The central spacer 52 can, in other embodiments, be oval or have any other shape. The central spacer 52 can also include a substantially concave portion formed thereon, as shown in FIG. 6A, to facilitate positioning thereof. In an exemplary embodiment, the superior and inferior faces of the central spacer 52 is concave to accommodate contact between the bony spinous processes and the central spacer 52.

Figure 6B:
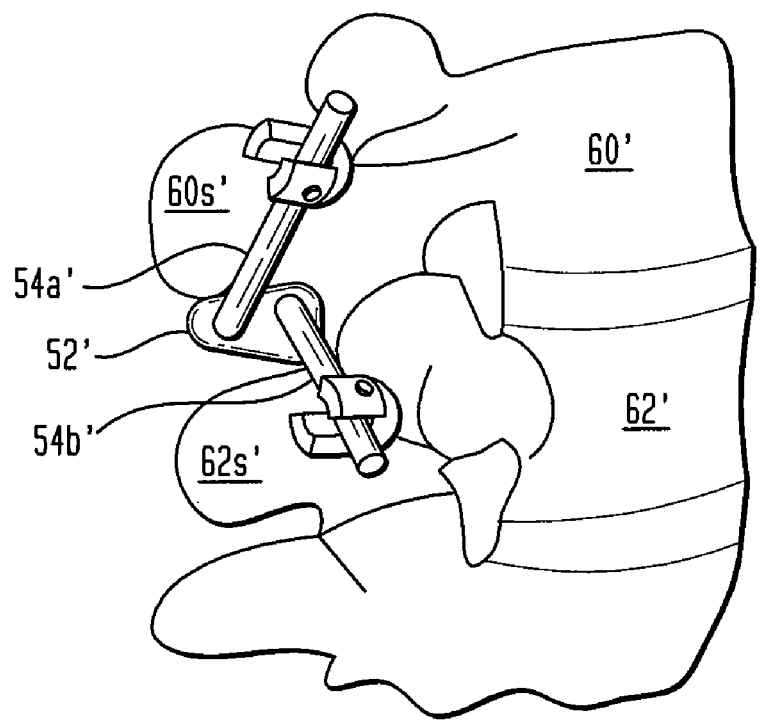
FIG. 6B is a side view of the spinal stabilization device of FIG. 6A coupled to adjacent vertebrae.

As indicated above, the central spacer 52 and the connectors 54a, 54b can have a variety of other configurations. FIGS. 6A and 6B illustrate another embodiment of a posterior stabilization device 50'. The device 50' is very similar to the embodiment shown in FIGS. 5A and 5B, however the connectors 54a', 54b' are substantially V-shaped with a straight base or central portion that extends through the central spacer 52' and opposed arms extending from the straight base. In use, the rotational movement between the connectors 54a', 54b' and the central spacer 52' allows flexion of the adjacent vertebrae. Furthermore, the deformable central spacer 52' allows controlled lateral bending, axial rotation, and anterior shear. The central spacer 52' can also be made from a variety of deformable materials. In an exemplary embodiment, the central spacer 52' is formed from a polymer, and more preferably a biocompatible polymer, such as a polyurethane, a composite reinforced polyurethane, a silicone, etc. A person skilled in the art will appreciate that the material can vary depending on the intended use. For example, a material can be selected, based on a patient's size and condition to have a particular stiffness.

Figure 7A:
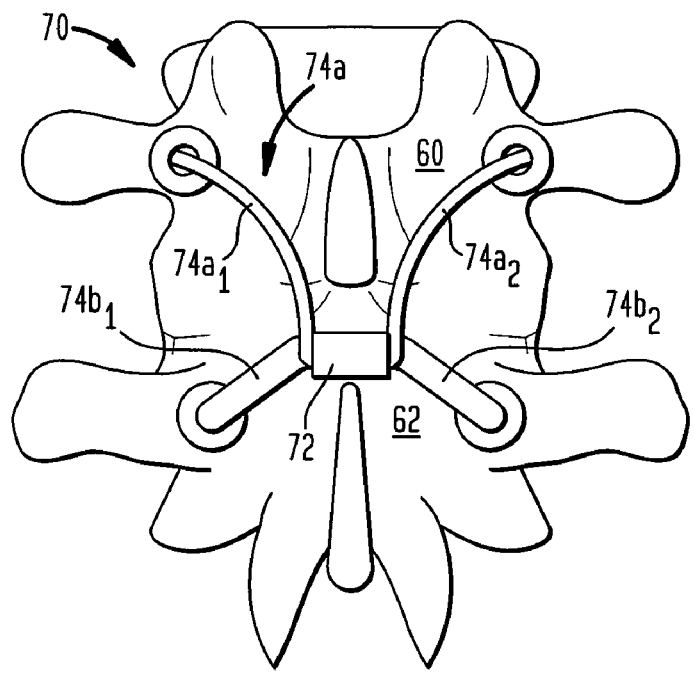
FIG. 7A is a posterior view of yet another embodiment of a spinal stabilization device coupled to adjacent vertebrae and having flexible connectors coupled to a rigid central spacer.
Figure 7B:
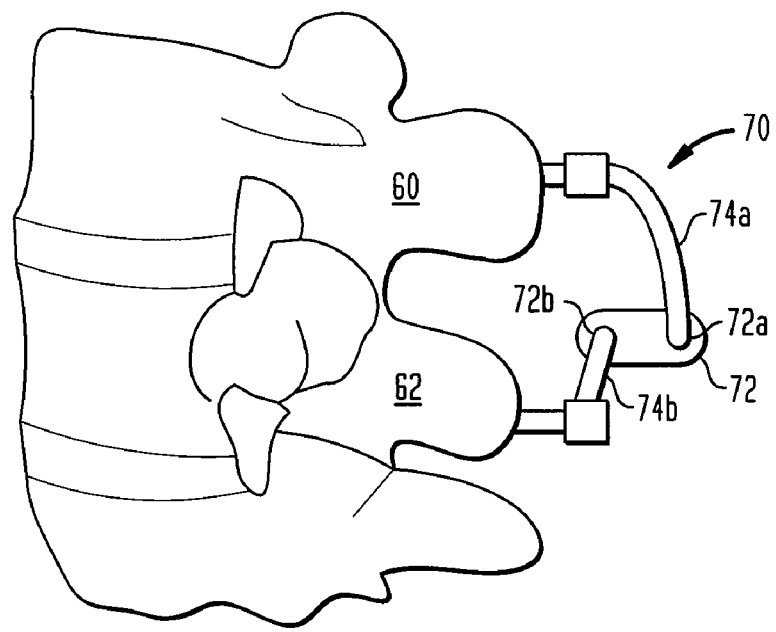
FIG. 7B is a side view of the spinal stabilization device and adjacent vertebrae shown in FIG. 7A.

FIGS. 7A and 7B illustrate another embodiment of a spinal stabilization device 70 having a central spacer 72 with superior and inferior connectors 74a, 74b rotationally coupled to the central spacer 72. In this embodiment, the superior connector 74a is substantially V-shaped with a straight base or central portion (not shown) that extends through the central spacer 72, and with opposed arms $74a_1$, $74a_2$ that extend from opposed ends of the central portion to mate to opposed lateral sides of the superior vertebra 60. As shown in FIG. 7A, the arms $74a_1$, $74a_2$ are convex relative to one another, i.e., they curve away from one another, such that they diverge from the central spacer 72. As shown in FIG. 7B, the arms $74a_1$, $74a_2$ are also curved in an anterior direction from the central spacer 72 toward the superior vertebra 60. The inferior connector 74b, on the other hand, has a substantially planar V-shaped configuration with a straight central portion (not shown) extending through the central spacer 72, and substantially straight arms $74b_1$, $74b_2$ extending from the central portion. The arms $74a_1$, $74a_2$ of the superior connector 74a and the arms $74b_1$, $74b_2$ of the inferior connector 74b may be permanently bent prior to the implantation or during the implantation to accommodate various patient anatomies. Moreover, the arms $74a_1$, $74a_2$ of the superior connector 74a and the arms $74b_1$, $74b_2$ of the inferior connector 74b may be elastically bent in the neutral position to provide preferential load due to the pre-stress of the arms. Similar to the embodiment shown in FIGS. 5A and 5B, a rotational or hinge joint is formed between each connector 74a, 74b and the central spacer 72 to allow and/or control movement of the adjacent vertebrae. The hinge joints are formed by bores 72a, 72b extending through the central spacer 72.

In use, during flexion and extension of the spine, the hinge joints can allow a large range of motion. The central spacer 72 can, however, be substantially rigid to function as a stop during extension, or in other embodiments it can be flexible to provide resistance to movement. In an exemplary embodiment, the central spacer 72 is substantially rigid and at least a portion of at least one of the connectors 74a, 74b is flexible to allow controlled extension, lateral bending, axial rotation, and anterior-posterior shear. The amount of resistance provided by the flexible connectors 74a, 74b can, however, be varied to obtain the desired result. For example, the diameter of the connectors 74a, 74b can be increased to increase the resistance to movement, or it can be decreased to decrease the resistance to movement. The shape and/or cross-sectional geometry of the connectors 74a, 74b can also be modified to allow a various degrees of movement in particular directions. For example, the connectors 74a, 74b can be configured to be highly flexible at locations which will provide minimal resistance to lateral bending, however they can be more rigid at locations which will provide maximum resistance to anterior-posterior shear.

Figure 8A:
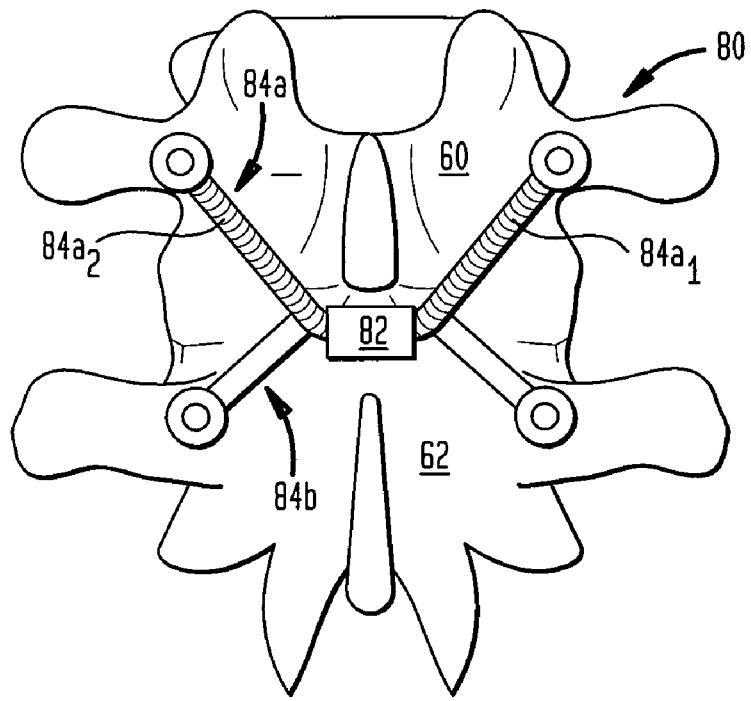
FIG. 8A is a posterior view of another embodiment of a spinal stabilization device coupled to adjacent vertebrae and having spring-rod connector arms coupled to a rigid central spacer.
Figure 8B:
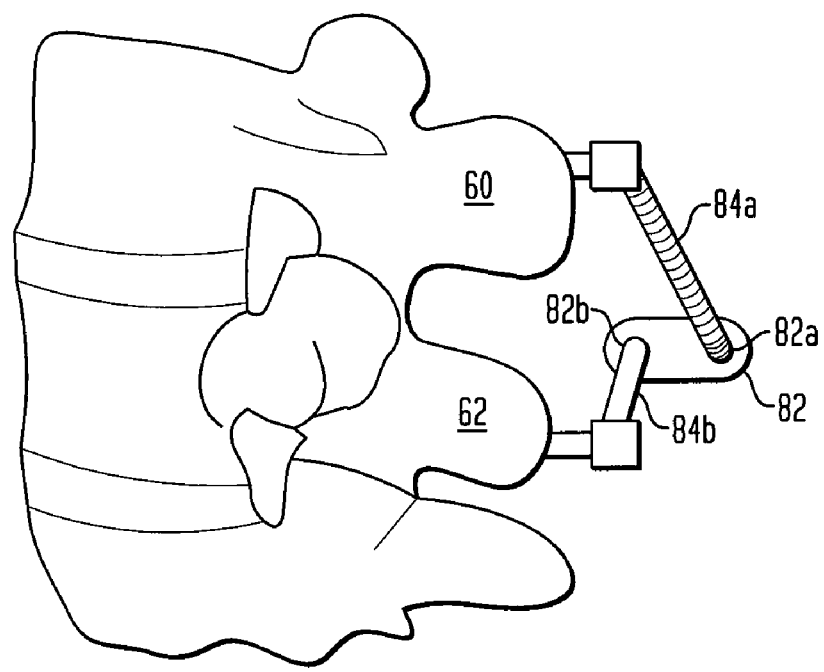
FIG. 8B is a side view of the spinal stabilization device and adjacent vertebrae shown in FIG. 8A.

FIGS. 8A and 8B illustrate another embodiment of a spinal stabilization device 80. This embodiment is very similar to the embodiment shown in FIGS. 7A and 7B, as it includes connectors 84a, 84b that are rotationally mated to a central spacer 82. In this embodiment, however, the arms $84a_1$, $84a_2$ of the superior connector 84a are in the form of spring-rods. In particular, the arms $84a_1$, $84a_2$ of the superior connector 84a each include a coiled portion to allow lateral bending, axial rotation, and anterior-posterior shear of the adjacent vertebrae 60, 62. The coiled portion can also function as a soft stop during extreme flexion, extension, and lateral bending. Such a configuration allows the central spacer 82 to be substantially rigid, thus forming a rigid bearing surface for the spinous processes or other posterior elements of the adjacent vertebrae 60, 62. The rotational or hinge joints between the connectors 84a, 84b and the central spacer 82 continue to allow flexion and extension, as with the previous embodiments. A person skilled in the art will appreciate that the spring-rods can alternatively or additional be used in the inferior connector 84b.

Figure 9A:
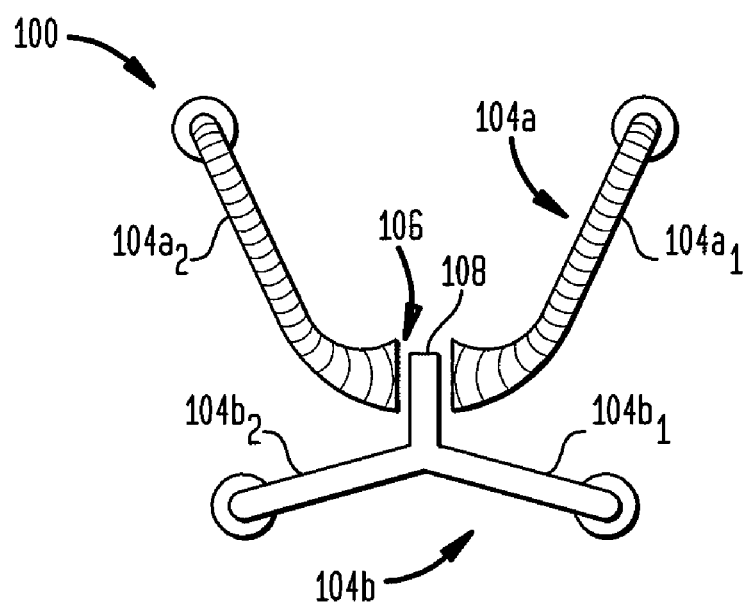
FIG. 9A is posterior view of another embodiment of a spinal stabilization device having a first connector with spring-rod arms, and a second connector slidably mated to the first connector.
Figure 9B:
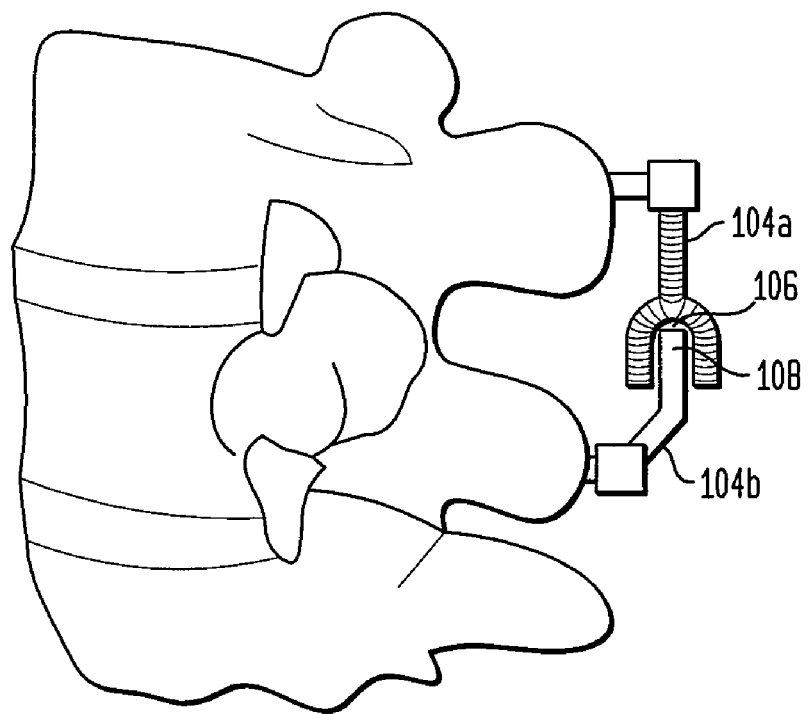
FIG. 9B is a side view of the spinal stabilization device shown in FIG. 9A.

A person skilled in the art will appreciate that other techniques, rather than a central spacer, can be used to form a linkage or a joint between the connectors. For example, the connectors can be directly coupled to one another by a rotating or sliding joint. FIGS. 9A and 9B illustrate one exemplary embodiment of a stabilization device 100 having a slider joint. As shown, the device 100 includes a superior connector 104a having spring-rod arms $104a_1$, $104a_2$ that mate to opposed lateral sides of a superior vertebra, and an inferior connector 104b having opposed arms $104b_1$, $104b_2$ that mate to opposed lateral sides of an inferior vertebra. Rather than having a central spacer between the connectors 104a, 104b, the superior connector 104a includes a slot or opening 106 formed therein and extending in a superior-inferior direction, and the inferior connector 104b includes an extension 108 that is slidably received within the slot or opening 106. As a result, the slider joint forms a bearing surface that allows flexion and extension, while the spring-rod arms of the superior connector 104a allow lateral bending, axial rotation, and anterior-posterior shear.

Figure 9C:
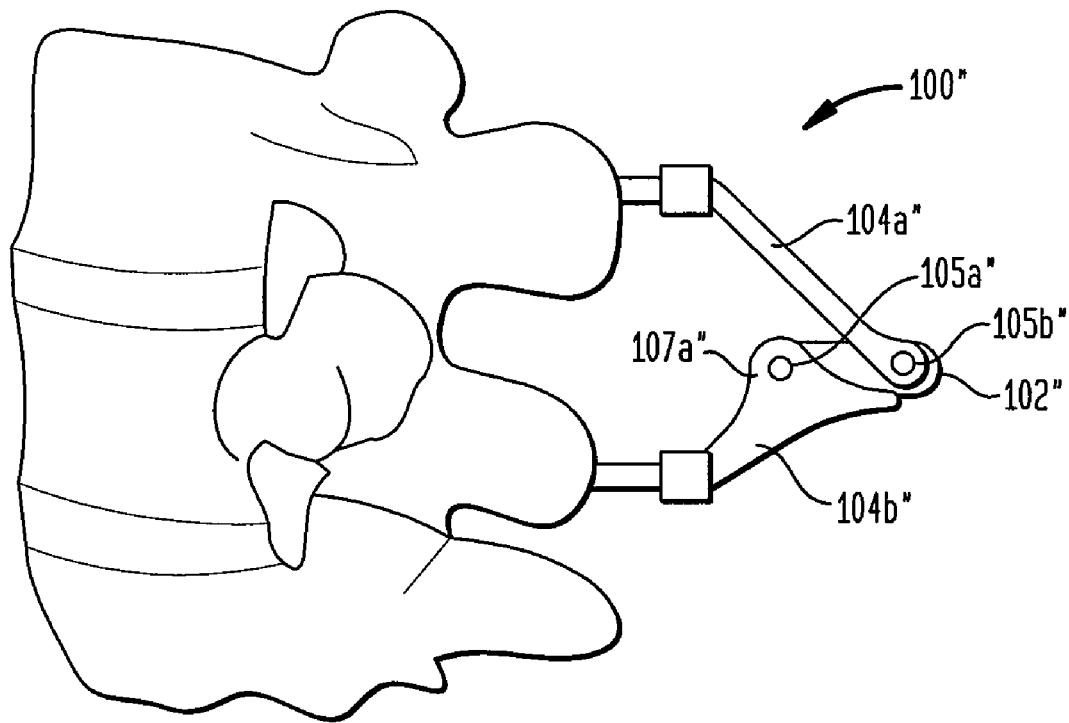
FIG. 9C is a side view of another embodiment of a spinal stabilization device having a first connector mated to a superior vertebra, and a second connector mated to an adjacent inferior vertebra and having a shelf formed thereon for receiving a portion of the first connector.
Figure 9D:
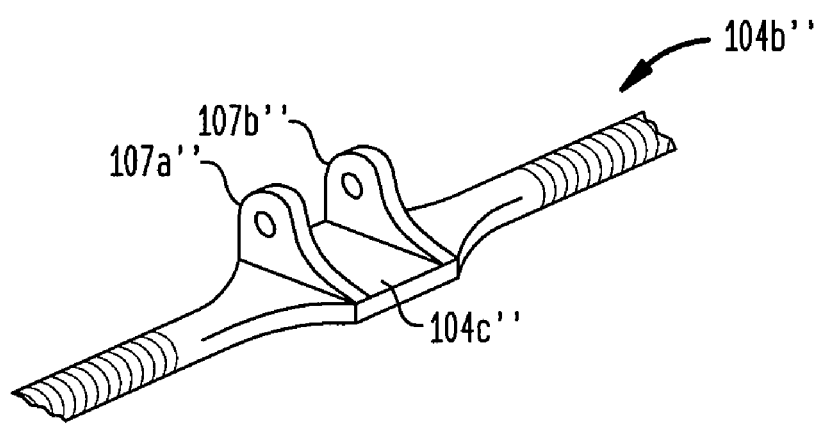
FIG. 9D is a perspective view of the second connector shown in FIG. 9C.

FIGS. 9C and 9D illustrate another embodiment of a stabilization device 100". In this embodiment, the inferior connector 104b" includes a shelf 104c" (FIG. 9D) formed thereon for seating a central spacer 102". The shelf 104c" can function as a stop during extension of adjacent vertebrae coupled to the device 100", and it can also include opposed sidewalls 107a", 107b" extending therefrom and configured to limit rotation of the central spacer 102". The central spacer 102" can be coupled to the superior connector 104a", and/or it can be coupled to the shelf 104c". As shown in FIG. 9C, the central spacer 102" is pivotally coupled to the shelf 104c" by a first hinge joint 105a", and the superior connector 104a" is pivotally coupled to the central spacer 102" by a second hinge joint 105b". In use, the hinge joints 105a", 105b" allow for flexion of the adjacent vertebrae coupled thereto. The arms on the superior and inferior connectors 104a", 104b" can also optionally be flexible to allow lateral bending, axial rotation, and anterior-posterior shear.

FIG. 9E illustrates a similar embodiment of a spinal stabilization device 100' that does not include a central spacer. In this embodiment, the device 100' includes a superior connector 104a' having spring-rod arms $104a_1'$, $104a_2'$ that mate to opposed lateral sides of a superior vertebra 60, and an inferior connector 104b' having opposed arms $104b_1'$, $104b_2'$ that mate to opposed lateral sides of an inferior vertebra 62. Rather than having a central spacer between the connectors 104a', 104b', the superior connector 104a' includes an extension arm 106' that extends in an inferior direction and that includes an upside down U-shaped terminal end 106t' formed therein and adapted to be positioned around the spinous process 62s of the inferior vertebra 62. In use, the extension arm 106' functions as a stop to limit extension of the adjacent vertebrae 60, 62. The extension arm 106' can also be slidably disposed through a central portion of the inferior connector 104b', and the U-shaped terminal end 106t' can be configured to abut against the inferior connector 104b' to function as a stop to limit flexion of the adjacent vertebrae 60, 62. The spring-rod arms of the superior connector 104a' will, however, allow some flexion, as well as lateral bending, axial rotation, and anterior-posterior shear.

The present invention also provides a cross-connector for maintaining a rigid connection between the arms of a connector or between two bone anchors. The cross-connector can have a variety of configurations, but in an exemplary embodiment it is adapted to couple to at least one of the connectors of a spinal stabilization device. A person skilled in the art will appreciate that the cross-connector can be used with virtually any spinal stabilization device, and that the devices shown in FIGS. 10A-10C are merely shown for illustrative purposes.

Figure 10A:
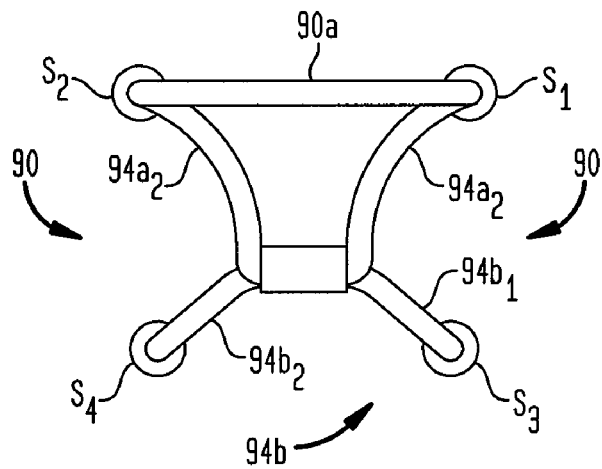
FIG. 10A is a posterior view of another embodiment of a spinal stabilization device having a cross-connector mated to opposed arms of a connector of the spinal stabilization device.
Figure 10B:
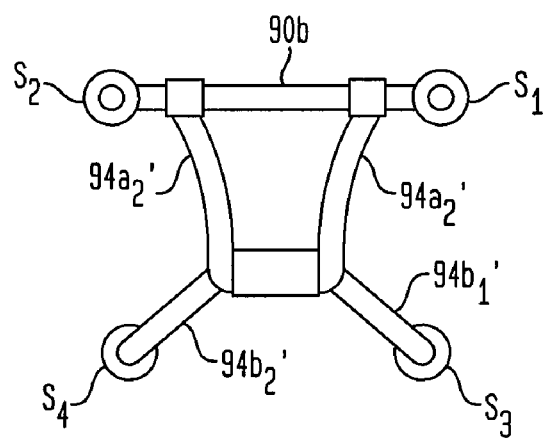
FIG. 10B is a posterior view of another embodiment of a spinal stabilization device having a cross-connector configured to mate to opposed lateral sides of a vertebra, and having a connector that mates to the cross-connector.
Figure 10C:
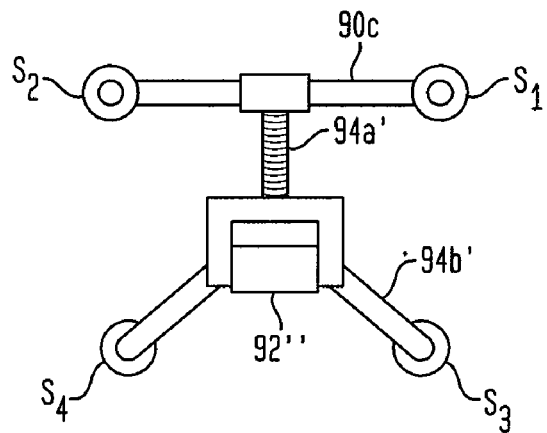
FIG. 10C is a posterior view of yet another embodiment of a spinal stabilization device having a spring-rod connector arm mated to a cross-connector configured to mate to opposed lateral sides of a vertebra.

FIG. 10A illustrates one exemplary embodiment of a cross-connector 90a. As shown, the cross-connector 90a is in the form of a rigid rod that extends between and mates to the bone-engaging elements, e.g., polyaxial bone screws $S_1$, $S_2$, for mating a spinal stabilization device 90 to adjacent vertebrae. As previously discussed, two bone-engaging elements, such as polyaxial bone screws $S_1$, $S_2$, can be used to mate the arms $94a_1$, $94a_2$ of a superior connector 94a to a superior vertebra, and two bone-engaging elements, such as polyaxial bone screws $S_3$, $S_4$, can be used to mate the arms $94b_1$, $94b_2$ of an inferior connector 94b to an inferior vertebra. The cross-connector 90a can extend between the two bone screws $S_1$, $S_2$ implanted in the superior vertebra, as shown, or it can extend between the two bone screws $S_3$, $S_4$ implanted in the inferior vertebra. Such a configuration prevents the bone screws $S_1$, $S_2$ from loosening relative to the vertebra, as the cross-connector 90a maintains the bone screws $S_1$, $S_2$ in a fixed position relative to one another.

While FIG. 10A illustrates the cross-connector 90a extending between two bone screws $S_1$, $S_2$, which are also coupled to a spinal stabilization device 90, the spinal stabilization device 90 can be coupled directly to the cross-connector, rather than the bone screws. For example, FIG. 10B illustrates a cross-connector 90b that extends between two bone screws $S_1$, $S_2$, and the arms $94a_1'$, $94a_2'$ of the superior connector 94a' are mated directly to the cross-connector 90b. Any type of mating element, such as a clamp, can be used to mate the arms $94a_1'$, $94a_2'$ of the superior connector 94a' to the cross-connector 90b. FIG. 10C illustrates another embodiment in which the superior connector 94a'' is mated directly to the cross-connector 90c that extends between the superior bone screws $S_1$, $S_2$. In this embodiment, the superior connector 94a'' is in the form of a spring-rod that extends in a superior-inferior direction and that rotationally mates to the central spacer 92''.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal stabilization device, comprising:
    a first connector having opposed terminal ends adapted to couple to opposed pedicles of a first vertebra, and a second connector having opposed terminal ends adapted to couple to opposed pedicles of a second adjacent vertebrae, at least a portion of at least one of the first and second connectors being elastically deformable to allow controlled lateral bending, axial rotation, and anterior-posterior shear between first and second adjacent vertebrae coupled thereto;
    a linkage having a first bore for receiving the first connector and a second bore for receiving the second connector such that the linkage is movably coupled to the first and second connectors to allow flexion of first and second adjacent vertebrae mated to the first and second connectors, wherein, when the first and second connectors are coupled to first and second vertebrae, the first bore is movable with motion of the vertebrae between a first position in which the first bore is positioned superior to the second bore, and a second position in which the first bore is positioned posterior to the second bore.

2. The device of claim 1, wherein first and second rotating joints are formed between the first and second connectors and the first and second bores, respectively.

3. The device of claim 1, wherein the linkage comprises a central spacer.

4. The device of claim 3, wherein the central spacer is adapted to be positioned adjacent to at least one spinous process of adjacent vertebrae coupled to the first and second connectors.

5. The device of claim 3, wherein the central spacer is rotatably mated to the first and second connectors by first and second hinge joints formed between the first and second connectors and the first and second bores, respectively.

6. The device of claim 5, wherein the first and second hinge joints are adapted to be spaced a distance apart from one another in a posterior-anterior direction when the device is coupled to adjacent vertebrae.

7. The device of claim 3, wherein the central spacer is elastically deformable.

8. The device of claim 3, wherein the central spacer is substantially rigid.

9. The device of claim 3, wherein the central spacer has a shape selected from the group consisting of a substantially triangular shape, a substantially oval shape, and a substantially cylindrical shape.

10. The device of claim 1, wherein at least one of the first and second connectors has a substantially curved configuration with opposed arms that are adapted to mate to opposed lateral sides of a vertebra.

11. The device of claim 1, wherein the elastically deformable portion has a symmetrical cross-sectional geometry.

12. The device of claim 1, further comprising a cross-connector adapted to mate to opposed arms of at least one of the first and second connectors.

13. The device of claim 1, further comprising a plurality of spinal anchors, each spinal anchor being configured to be implanted in a vertebra to fixedly mate a terminal end of one of the first and second connectors to the vertebra.

14. A spinal stabilization device, comprising:
    a superior connector rod having opposed arms with terminal ends configured to mate to opposed pedicles of a superior vertebra;
    an inferior curved connector rod having opposed arms with terminal ends configured to mate to opposed pedicles of an inferior vertebra;
    a wedge-shaped central spacer configured to be positioned between superior and inferior spinous processes of superior and inferior vertebrae and having a posterior bore extending laterally therethrough and an anterior bore extending laterally therethrough, the superior connector rod extending through the posterior bore to form a first rotational joint between the superior connector rod and the central spacer, and the inferior connector rod extending through the anterior bore to form a second rotational joint between the central spacer and the inferior connector rod, the first and second rotational joints being configured to rotate during movement of the superior and inferior vertebrae.

15. The device of claim 14, further comprising first and second superior spinal anchors configured to be implanted in a superior vertebra to fixedly mate opposed terminal ends of the superior connector to the superior vertebra, and first and second inferior spinal anchors configured to be implanted in an inferior vertebra to fixedly mate opposed terminal ends of the inferior connector to the inferior vertebra.

16. The device of claim 15, wherein the terminal ends of the first connector rod are configured to be received in rod-receiving recesses faulted in the first and second superior spinal anchors, and the terminal ends of the second connector rod are configured to be received in rod-receiving recesses formed in the first and second inferior spinal anchors.

* * * * *